United States Patent [19]
Guillouzo et al.

[11] Patent Number: 5,859,192
[45] Date of Patent: Jan. 12, 1999

[54] FACTORS FOR CELLULAR FUNCTIONAL REGULATION AND BIOLOGICAL APPLICATIONS THEREOF

[75] Inventors: Christiane Guillouzo; Anne Corlu, both of Rennes; Bernard Kneip, Liffre, all of France

[73] Assignee: Cabinet Armengaud Aine, Paris, France

[21] Appl. No.: 204,417

[22] PCT Filed: Sep. 16, 1992

[86] PCT No.: PCT/FR92/00867

§ 371 Date: Apr. 19, 1994

§ 102(e) Date: Apr. 19, 1994

[87] PCT Pub. No.: WO93/06134

PCT Pub. Date: Apr. 1, 1993

[30] Foreign Application Priority Data

Sep. 16, 1991 [FR] France ................................. 91 11389

[51] Int. Cl.⁶ .......................... C07K 14/475; C12N 15/12
[52] U.S. Cl. .......................... 530/350; 530/328; 530/329; 530/330; 530/395; 530/412; 530/413; 435/325; 435/375; 536/23.5
[58] Field of Search ..................... 530/350, 395, 530/412, 413, 328, 329, 330; 514/2, 8, 12, 4; 435/240.2, 252.3, 320.1, 325, 375; 536/23.5

[56] References Cited

U.S. PATENT DOCUMENTS 3,816,263  6/1974  Rabin et al. ......................... 195/103.5

OTHER PUBLICATIONS

Curula et al. (1990) Proc. Natl. Acad. Sci. U.S.A. vol. 87, pp. 6378–6382.

Scott et al. (1990) Science. vol. 249, pp. 386–390.

Devlin et al. (1990) Science vol. 249, pp. 404–406.

Tingstroem et al, "Distribution and Dynamics of Cell Surface–Associated CellCAM 105 in Cultured Rat Hepatocytes", Chemical Abstracts 112(5):392, abstract No. 33895e (1990).

Hopf et al, "Glycoproteins of Rat Liver Plasma Membranes: Their Hepatocellular, Intestinal and Renal Expression in Rat, Rabbit and Human", Chemical Abstracts 114(19):503, abstract No. 182615g (1991).

Baffet et al, "Distinct Effects of Cell–Cell Communication and Corticosteroids on the Synthesis and Distribution of Cytokeratins in Cultured Rat Hepatocytes", Biological Abstracts 92(9):AB–291, abstract No. 97586 (1991).

Fraslin et al, "Dependence of Hepatocyte–Specific Gene Expression on Cell–Cell Interactions in Primary Culture", Chemical Abstracts 104(5):395, abstract No. 32390j (1986).

Gallin et al, "Antibodies to liver cell adhesion molecular perturb inductive interactions and alter feather pattern and structure", Proc. Natl. Acad. Sci. USA 83:8235–8239 (1986).

Corlu et al, "A Plasma Membrane Proteins Is Involved in Cell Contact–mediated Regulation of Tissue–specific Genes in Adult Hepatocytes", The Journal of Cell Biology 115(2):505 (1991).

*Primary Examiner*—John Ulm
*Assistant Examiner*—Prema Mertz
*Attorney, Agent, or Firm*—Nixon & Vanderhye P.C.

[57] ABSTRACT

The invention relates to proteins characterized in that they are proteins for communication between cells of a given type and the contiguous or proximal heterologous cells.

11 Claims, 21 Drawing Sheets

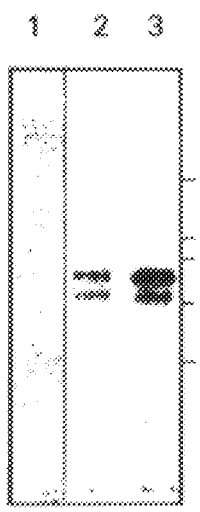
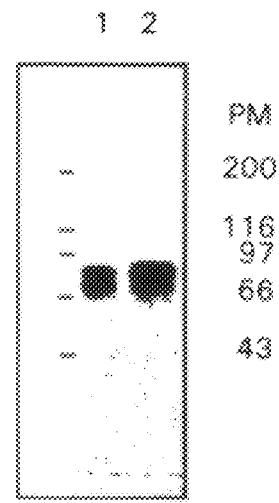
Fig.6A　　Fig.6B
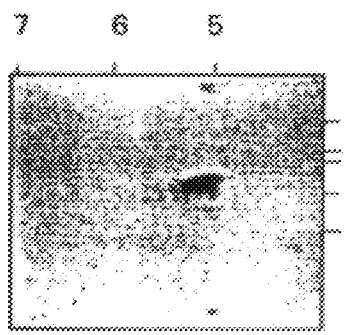
Fig.6C
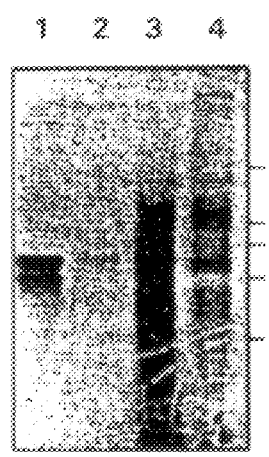
Fig.6D

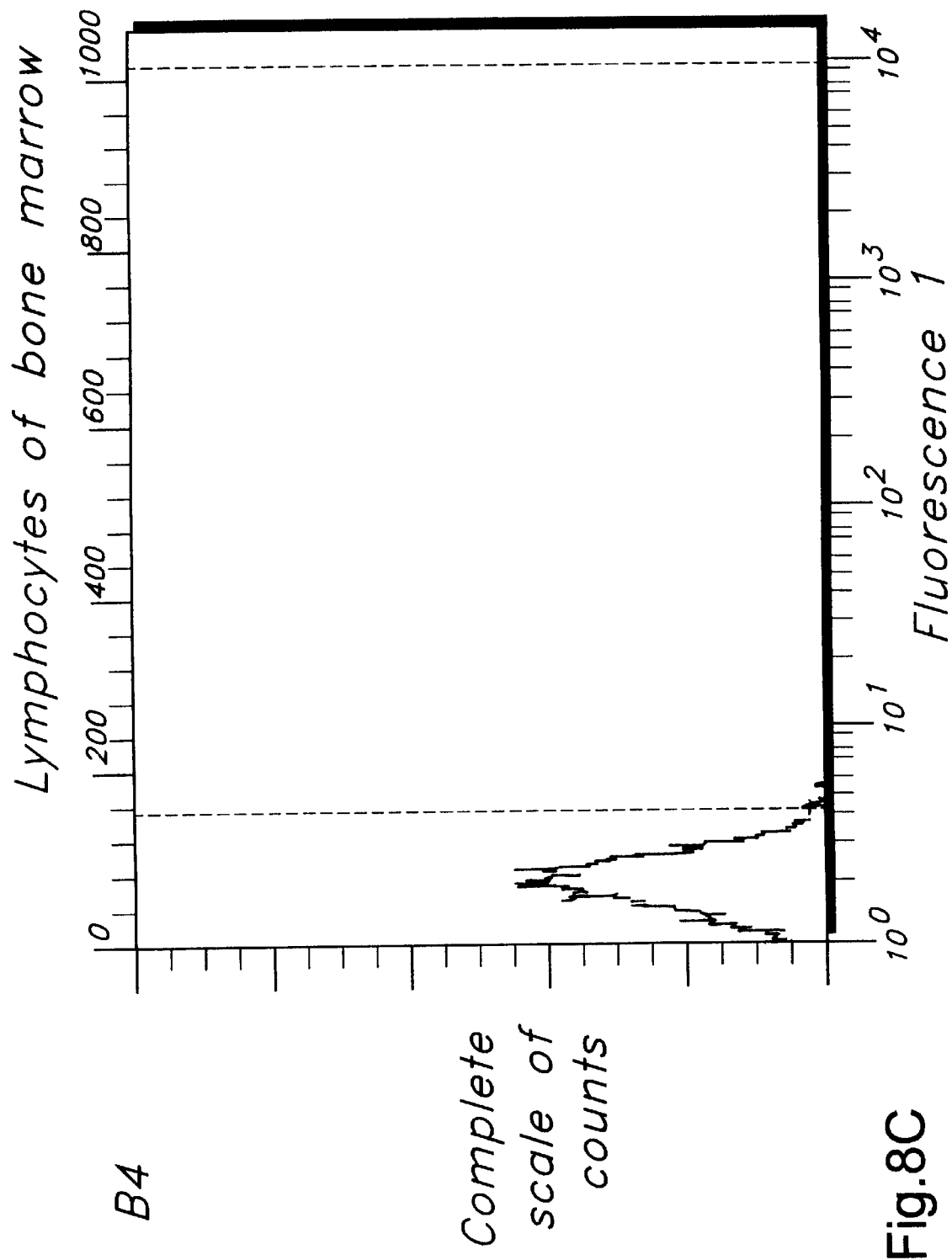

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Leu  Pro  Gln  Asp  Met  Ser  Gly  Phe  Gln  Lys
1                   5                        10

( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ile  Asn  Pro  Thr  Asp  Glu  Ser
1                   5

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single -continued (D) TOPOLOGY: linear (i i) MOLECULE TYPE: peptide (x i) SEQUENCE DESCRIPTION: SEQ ID NO:3:

```
Gly  Leu  Gln  Met  Lys
 1                    5
```

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:4:

```
Asp  Met  Val  Glu  Phe  Arg
 1                    5
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

```
Asp  Met  Val  Glu  Phe
 1                    5
```

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:6:

```
Ile  Asn  Pro  Xaa  Asp  Glu  Ser
 1                    5
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:7:

```
Asp  Met  Val  Glu  Phe  Xaa
 1                    5
```

FACTORS FOR CELLULAR FUNCTIONAL REGULATION AND BIOLOGICAL APPLICATIONS THEREOF

This application is the U.S. national phase of PCT/FR92/00867 filed Sep. 16, 1992.

A subject of the invention is proteins which, in particular, are capable of constituting factors for cellular functional regulation and their biological applications.

The fundamental role of interactions and communications between cells is known.

Cell-cell interactions assume a major importance in the development and organisation of multicellular organisms, as well as in their physiology and their pathology.

It is generally accepted that these interactions take place due to the effect of circulating soluble factors, but also by means of cell adhesion molecules (CAM), matrix support adhesion molecules and molecules constituting functional structures between the cells.

These molecules provide at the same time, regulation of genesis during the early stages of development, including moreover the primary processes such as cellular proliferation and migrations. They give rise to signals which lead to differential expression of genes and in this way, to embryonic induction (see in particular Gallin et al., Proc. Natl. Acad. Sci. USA. 83:8235–8239, 1986; Edelman, Immunol. Rev. 100:11–45, 1987; Jessel, Neuron. 1:3–13, 1988). Although the role of these molecules has been well established, the molecular mechanisms involved in these coordinated regulations are however still largely unexplained.

The communications between cells also play an important role in maintaining the differential expression of genes of mature cells of adult tissues, as has been shown in particular in work carried out on the peripheral and central nervous systems (see, in particular, Rathjen et al., J. Cell. Biol. 104:343–353, 1987 and Seilheimer et al., J. Cell. Biol. 109: 3095–3103, 1989). Another example of great interest in this respect is provided by the adult liver. In fact, it is noted that the dissociation of hepatic tissue in order to isolate the hepatocytes leads to a strong reduction of the transcription of genes coding for the specific functions of the liver (see Clayton et al. Mol. Cell. Biol. 5:2623–2632, 1985). In addition, it was noted that the establishment of homotypic interactions in culture, i.e. between hepatocytes, does not permit the preservation of their adult phenotype, while the proteoglycans induce the formation of functional junctional structures and restore the transcription of specific mRNA's in primary cultures. These results taken together tend to demonstrate the major role of non-parenchymatous cells on the differential transcription of specific genes of the liver in adult hepatocytes.

Some of the co-inventors of the present Application have described in the Patent FR 8307148 of 29th Apr. 1983, in the name of INSERM, a process for the co-culture of adult human hepatocytes with a heterologous cell population, but of hepatic origin. During the co-culture, the establishment of contacts between the two cell populations was noted. It follows that the functional activities of the hepatocytes were maintained over several weeks. During the co-culture, the secretion and deposition of various components of a matrix was observed giving a complex extracellular matrix network which surrounds and covers the hepatocyte colonies and in a parallel and coordinated manner, activation of the expression of specific genes of the liver.

The inventors have used this system of the co-culture of hepatocytes to study the causal relationships between the different biological events which lead to a stable differentiation of hepatocytes in the adult liver.

An immunological approach to this problem allowed them, by using a determined monoclonal antibody, to reveal the critical role played in this respect by a membrane protein.

In pursuing this work, the inventors noted that cells other than hepatocytes, in tissues other than liver tissues, contained in their membrane proteins of this type which are also recognised by the monoclonal antibody in question.

Therefore an aim of the invention is to provide proteins which are involved in a major way in the interactions and communications from cell to cell.

More especially it aims to provide proteins for the regulation of differentiated cells, or for cells in the process of differentiation.

Moreover, the invention relates to the biological application of these proteins, in particular as factors for functional regulations and as markers of cellular differentiation.

The proteins of the invention are characterized in that they contain or are constituted by an amino acid sequence capable of reacting specifically with a monoclonal antibody such as that obtained by the immunization of an animal with rat epithelial cells of hepatic origin, followed by stages of fusion and cloning carried out according to standard techniques, in particular the monoclonal antibody secreted by the strain of hybridoma deposited at the D.S.M (Deutsche Sammlung von Mikroorganismen und Zellkulturen GmbH) on 19th Jun. 1991 under the No. DSM ACC 2011.

In an unexpected fashion, it appears that such proteins are capable of playing a critical role in cellular communication, and in particular in the specific recognition and interaction of different cell populations and lead to the active transcription of certain genes and the expression of functions characteristic of a given tissue. They constitute proteins for the communication between the cells of a given type and contiguous or joined heterologous cells. In fact they turn out to be capable of ensuring the transmission of a signal or signals from one cellular type to another cellular type which may be contiguous or proximal.

As regards tissue distribution in the adult state, the proteins of the invention are expressed in particular at the level of the liver, the exocrine pancreas, the testicles, the ovaries and the hematopoietic tissues.

At the cellular level in the liver, they are characterized in that they are membranous and polarized towards the sinusoidal pole of normal adult hepatocytes.

This polarity may disappear in hepatoma cells, foetal liver and regenerating liver.

The proteins according to the invention are also characterized in that they are expressed in particular by hepatocytes, epithelial cells of the biliary ductules, endothelial cells, Ito cells and macrophages.

They are also characterized in that in the testicles they are expressed at the level of the seminiferous tubules by Sertoli cells (so-called nursing cells) and spermatocytes at a precise stage of maturation, at the end of the leptotene and zygotene stage.

Moreover, they are characterized in that in the ovary they are expressed by the ovocytes and the follicular cells (nursing cells) which surround them, uniquely at a very precise stage of maturation, just like the spermatocytes in the testicles.

The studies carried out on co-cultures of hepatocytes and epithelial cells from rat's liver (abbreviated to RLEC), according to the process of the French Patent mentioned above, have shown the involvement of specific proteins, of the type of those defined above, in the interactions between these two cell populations.

These specific proteins are also involved in the functional activity of germ cells.

The studies carried out on co-cultures of Sertoli cells and epithelial cells of the liver, advantageously carried out according to the process of the French Patent above, have shown the involvement of proteins of the type defined above in the differentiation of Sertoli cells.

The proteins of the inventions are characterized in that they are expressed in hematopoietic tissues (bone marrow, thymus, lymph nodes and spleen) and in the blood, (by the monocytes, granulocytes, erythrocytes and lymphocytes).

The studies carried out on co-cultures of epithelial cells of the liver and hematopoietic cells have shown the involvement of proteins in the proliferation and maturation of these hematopoietic cells.

The direct involvement of proteins has moreover been confirmed by revealing the presence of the proteins of the invention in cells containing the stromal tissue of bone marrow and by the obtaining of a maturation of the hepatocytes when they are co-cultured with stromal cells.

In these different cases, the proteins of the invention constitute the glycoproteins of the membrane.

These proteins are more particularly characterized in that they are formed by an amino acid sequence having a molecular weight (MW) of approximately 85000 daltons, as measured by electrophoresis in polyacrylamide denaturing gel.

This sequence, according to one provision of the invention, contains one or more of the following concatenations, namely: L-P-Q-D-M-S-G-F-Q-K (SEQ ID NO:1), I-N-P-(T)-D-E-S (SEQ ID NO:2), G-L-Q-M-K, (SEQ ID NO:3) D-M-V-E-F-(R) (SEQ ID NO:4)

Conventionally, the letters used have the following meanings:
L=leucine, P=proline, Q=glutamine, D=aspartic acid,
M=Methionine, S=serine, G=glycine, F=phenylalanine,
K=lysine, I=isoleucine, N=asparagine, T=threonine,
E=glutamic acid, V=valine, R=arginine.

According to another aspect, the proteins of the invention revealed in the co-cultures of hepatocytes are membrane proteins having a pI from about 4.9 to 5.1 by analysis on two-dimensional gel.

According to a variant, these proteins are presented in a form having a MW of about 73,000 daltons, having the epitope recognized by the monoclonal antibody (or abbreviated to MAb) defined above, corresponding to truncated membrane proteins. In particular, these proteins have a pI of the order of 5.2.

It should be noted that the MW of the protein sequences can vary appreciably from one species to another, even from one tissue to another and from one cell type to another. Moreover, they have one specific region or domain of one cell type for a given tissue, of a given species.

According to one of the various aspects outlined above, these proteins of the invention are also characterized in that they are constituted by one single protein chain.

The involvement of these proteins can be appreciated with regard to the alteration of functional activity of mature hepatocytes when a monoclonal antibody which specifically recognizes them is added to the co-culture, compared with the functional activity of co-cultures which have not been treated with MAb.

This alteration is observed with regard to parameters which are significant for the good maintenance of a differentiation stage in the co-culture, namely, the survival of the hepatocyte for several weeks, the production of albumin, the presence of high levels of liver-specific mRNA, the characteristic organization of the components of the cytoskeleton and the deposition of fibres of the extracellular matrix. As shown in the examples given hereafter, the immunoreaction of the proteins of the invention with the monoclonal antibody results in the loss of the adult phenotype of the hepatocytes, and as in pure cultures, by a survival time reduced to about 5 or 6 days, a rapid diminution of the secretion of albumin with a level lower than about 50% of normal production, accompanied by a diminution of the level of corresponding mRNA's and mRNA's of other genes specific to the liver.

It is noted that, as in pure cultures, the hepatocytes of co-cultures treated with the monoclonal antibody in question synthesize I$\alpha_1$ procollagen which does not polymerize.

These changes correspond to an almost complete loss of deposition of extracellular matrix.

They also coincide with an incapacity by the hepatocytes to develop a cytoskeleton architecture characteristic of a differentiated phenotype.

The results obtained on hepatocytes reveal the role of the proteins of the invention in the functional regulation of cells.

In particular, the coordinated effects, induced or mediated, by these proteins, the expression of specific genes of tissues, the organization of the proteins of the cytoskeleton and the deposition of an extracellular matrix will be measured.

According to another aspect of the invention, the proteins in question are characterized in that they are glycoproteins.

According to yet another aspect, the proteins of the invention are characterized in that they are constituted as such by the active part of the proteins defined above, i.e. the part responsible for the communication between the cells of a given type and the contiguous or proximal heterologous cells.

In particular, the invention relates to the glycosylated part of the proteins defined above.

According to yet another aspect of the invention, the proteins which are active vis-à-vis cell-cell regulation are recombinant proteins and contain at least the active part mentioned above.

According to another variant of the invention, the proteins of the invention are analogues of the proteins defined above, i.e. their amino acid sequence can differ from that of the reference active protein sequence by one or more amino acids deleted and/or replaced and/or substituted, so long as these changes do not alter the properties defined above.

It should be noted in this respect that the term protein as it is used in the description and the claims designates both proteins as obtained by a synthetic route and proteins in native form or recombinant form, the active parts of these proteins and their analogues as defined above.

The invention also relates to a process for obtaining the proteins defined above.

This process includes putting an extract of liver membranes in contact with a monoclonal antibody capable of specifically recognizing a surface protein of epithelial cells of rat's liver or a Fab fragment having such a property.

The liver membranes are advantageously solubilized with an agent which has the effect of lysing them, in particular a detergent agent such as Triton X100.

For the stage of putting into contact the monoclonal antibody or the Fab fragment is advantageously coupled to a support, more especially a support which can be used in a column such as Sepharose 4B.

The sought proteins selectively fix themselves to the antibody by immunoreaction and are then eluted. To this end it is advantageous to proceed with an increase of the pH of the buffer.

Diethylamine of pH 11.5 containing 0.05% Triton X100 can be mentioned as an appropriate buffer.

For the purposes of purification the collected eluate containing a given protein is put in contact with a selective adsorbent which allows the elimination of proteins with a molecular weight identical to that of the sought protein but with different iso-electric points, then the protein is desorbed using an appropriate buffer and it is recovered from the eluate.

The proteins of the invention can also be purified by a polyclonal antibody induced in a standard fashion by the immunization of an animal. In a general way, the polyclonal antibodies directed against the proteins of the invention in native or recombinant form, or their active part, or their analogues as defined above, are also included within the scope of the invention.

Naturally, any tissue other than liver membranes giving rise to an immunological reaction with the antibodies as defined above can be used to obtain the proteins of the invention. It should be noted that recognition by the antibody is not specific to the species.

The monoclonal antibody used as an identification tool for the proteins is that obtained by secretion from the hybridoma strains resulting from the fusion of an immortal cell of non-secreting myeloma with a cell producing an antibody directed against a surface protein of epithelial cells of rat's liver.

The fusion stage of the two cell types is notably carried out according to the most currently-used technique, namely that of Köhler and Milstein, Nature, vol. 256, p. 495, 1975.

The antibody-producing cells are splenocytes. These cells are recovered after immunization in vivo of the animal with a cellular suspension of living RLEC's.

The immortal cells are cells of the non-secreting myeloma, which allows hybridomas which only secrete the immunoglobulin with the specificity of the producer cell to be obtained. In a standard fashion cells of the $SP_2/O$—Ag myeloma are used.

In accordance with the standard technique the hybridomas obtained are cultured and cloned according to the process of limited dilution. Advantageously hybridomas are selected of which the culture supernatants produce immunoglobulins, using a standard immunofluorescence test.

A second selection process is used on the positive clones retained at the end of the previous stage, only retaining the clones which are capable of recognizing a protein of the plasmatic membrane by giving rise to a reaction of antigen-antibody type but which do not react with two types of non-hepatic cells, namely the endothelial cells of the cornea and the fibroblasts of human skin.

The monoclonal antibodies recovered can be used as they are or are purified, for example on an affinity column, and stored by freezing or optionally lyophilized.

Quite particularly the invention relates to the monoclonal antibody L8 the production method of which is mentioned in the examples.

The hybridoma strains producing the monoclonal antibodies defined above, as well as the process for obtaining them, including the fusion and selection stages defined above related to the monoclonal antibodies, are also included within the scope of the invention.

According to a variant of the invention, the proteins recognized by the monoclonal antibodies in the process of the invention correspond to recombinant proteins containing or partially or totally formed by the active part vis-à-vis cell-cell regulation.

By operating according to the standard techniques of gene transfer in genetic engineering, these proteins are produced in hosts, transformed by the introduction of expression or cloning vectors, in particular plasmids, containing fragments of the gene coding for the sought amino acid sequences.

These fragments are introduced by ligation in an appropriate site of the chosen vector.

As examples, hosts which are appropriate for the implementation of the invention include bacteria, yeasts or also cells of arthropods, vertebrates or plants.

The proteins expressed are recovered from the culture medium, after lysis of the bacteria, and purified.

According to yet another variant, the proteins of the invention are formed by the active part as already defined, or by the sequences given above, or are analogues of these proteins, these sequences or their active part. These proteins are obtained by genetic recombination or peptide synthesis according to standard techniques.

The implementation of these techniques leads to the development of tools which constitute new products. Therefore, the transformed cellular hosts, the expression vectors such as plasmids and DNA fragments as mentioned above are included within the scope of the invention.

According to another variant, the proteins of the invention, more particularly the active parts, or the fragments of sequences, are obtained by synthetic route. Advantageously, by operating according to the usual techniques, a determined peptide chain is formed using a syntheziser.

Taking into account their role in the communication and in the interactions between cells, the proteins of the invention are of great interest as a factor for the functional regulation of target cells in a given tissue.

In particular, the invention relates to their application in cellular cultures with a view to ensuring the restoration and maintenance of the functional activity of a given type of cells.

Advantageously, the cultures are carried out under the usual conditions and the protein is added to the medium.

As mentioned in the examples, the proteins of the invention play a major role in the hepatocytary operation in culture.

More particularly, the invention therefore relates to a process for the culture of hepatocytes, in particular human hepatocytes, including the application of a protein as defined above by replacing the RLEC's used in the process of the Patent already mentioned.

In another application as a factor for functional regulation, the proteins of the invention are used to restore or maintain the operation, for example, of hematopoietic cells in culture.

In this way, they can be used to favour the proliferation of hematopoietic cells in such a way as to constitute a supplementary treatment for patients suffering from aplasia, having lost, after chemotherapy or radiotherapy, their progenitors or a large part of their hematopoietic cells.

Before proceeding with these treatments, bone marrow cells or hematopoietic cells are removed from the patient or from compatible donors, they are cultured with the proteins of the invention or with cells which express them. The cells produced are then injected into the patient.

Advantageously, the elements for such cell cultures are available, conforming to the invention in the form of kits, which also allow the establishment of cell banks from which it is possible to regularly produce hematopoietic cells, progenitors and precursors which can be injected into patients, in the absence of compatibility problems.

Moreover, the invention relates to a kit containing the protein as defined above and the reagents or a part of the reagents necessary for the production of a given cell culture. Advantageously, the kit also contains the cells concerned.

The proteins of the invention are also useful as cellular markers.

These markers allow studies of the fundamental mechanisms to be carried out.

In particular, they are of application in pharmacopoeia constituting cellular models for the study of the toxicity or myelotoxicity of medicinal molecules and/or for the analysis of the products of metabolization.

Advantageously, the products of the invention constitute markers of cellular differentiation, cellular polarity or also cellular distribution.

Revealing the presence of the proteins of the invention is advantageously carried out using polyclonal or monoclonal antibodies, developed according to standard techniques, which are capable of specifically recognizing these proteins.

Advantageously, it is an antibody directed against at least one part of the region or domain of the specific amino acid sequence of a cell type of a given tissue, of a given species.

According to a variant, these antibodies are characterized in that they are capable of recognizing by giving rise to an antigen-antibody type reaction, at least one of the fragments given above, of the following sequences:

L-P-Q-D-M-S-G-F-Q-K (SEQ ID NO:1), I-N-P-(T)-D-E-S (SEQ ID NO:2), G-L-Q-M-K (SEQ ID NO:3), D-M-V-E-F-(R) (SEQ ID NO:4)

As already emphasized, the proteins of the invention allow a given differentiation stage to be characterized.

Therefore, according to an aspect of major interest, the proteins of the invention constitute germ cell markers at a precise stage of differentiation at the adult stage, but also during development.

Tests carried out on cultures of testicle cells have shown that the proteins of the invention are expressed at the level of the seminiferous tubules by the Sertoli nursing cells and the spermatocytes at a very precise stage of maturation (see article by R. A. Hess in Biology of Reproduction 43, 525–542, 1990).

The antibodies directed against these proteins, advantageously formed, according to the standard techniques against a purified protein of human origin, and more particularly against the specific region of this protein, for this type of tissue, constitute tools which are particularly invaluable for carrying out high precision diagnostics or cellular selections.

They are therefore useful for the characterization of semen analyses.

The proteins of the invention are also present in the ovocytes and follicular cells which surround them only in the mature follicles which are recognizable by the formation of the atrium.

The application of antibodies directed against these proteins allows the recognition of mature ovocytes which are the only ones capable of being fertilized.

Therefore the invention relates to the application of these antibodies as bioreagents for the in vitro diagnosis in a biological sample of the presence of male germ cells or female germ cells at precise stages of maturation as indicated above, with a view to their characterization and/or their selection.

For this application the antibodies are free. In a variant they are fixed to a non-immunogenic support.

According to another aspect which is of great interest, the proteins of the invention constitute blood cell markers.

Therefore the invention also relates to the antibodies directed against the specific proteins of different blood cells.

In a general manner, the method according to the invention for in vitro diagnosis of the presence of proteins as defined above in a biological sample or of cells is characterized in that it includes the following stages:

the sample to be analyzed or the cells are put in contact with a preparation of an antibody or a Fab fragment, as defined above, immobilized on a solid support, under appropriate conditions for the production of an antigen-antibody complex with the said proteins, when they are present in the sample, then the formation of such an antigen-antibody type complex is revealed by advantageously operating according to the usual techniques.

Cytofluorometric techniques can, for example, be used.

This detection method allows the presence of these membrane proteins in the sample under test to be revealed quickly and with great sensitivity.

Thus these proteins constitute for example markers for the differentiation on the one hand of Sertoli cells and spermatocytes at a given stage, and on the other hand, of ovocytes which are also at a precise stage of maturation, for localizing them and even for selectively collecting them and quantifying them.

The usefulness of this method will be measured within the scope of in vitro fertilizations for the selection of mature ovocytes or for the culture of ovocytes with a view to storage and/or maturation in vitro.

These immunohistological applications based on the early role played by the proteins of the invention in cellular differentiations, extend to all tissues which are able to express them at the early embryonic stage or at later stages of development.

They allow the study of the specificity of expression in the adult state of the cells of a given tissue.

The above method is also applicable for carrying out a selection among cellular populations of those cells which express the proteins of the invention.

It can also advantageously be applied to the diagnosis and monitoring of any hemopathy, in particular aplasias by allowing the detection of a missing blood element, an anomaly at the level of the stromal cells or loss of the progenitors of hematopoietic cells.

Also the invention relates to a kit for revealing said proteins with a view to the in vitro diagnosis of their presence in a biological sample or for carrying out a cellular selection.

This kit is characterized in that it contains:
  an appropriate solid phase serving as a support for the determination, such as a microtitration plate,
  a preparation of the antibody or the Fab fragment, free or immobilized, as defined above,
  appropriate buffer solutions for the immunological reactions and for the detection reactions.

According to another aspect of the invention, the recognition of native proteins by the antibodies against these proteins, allows the application of these antibodies as a contraceptive vaccine.

The administration of these antibodies to mice can lead to an inhibition of fertility during the treatment.

Therefore the invention also relates to a contraceptive vaccine characterized in that it contains, in combination with an inert vehicle, an antibody directed against the proteins, or parts of the proteins of mature ovocytes or spermatocytes as defined above, more particularly against at least one part of the region of these proteins specific for the tissue in question.

The rest of the description includes examples in which the results obtained with hepatocytes as cell type, are given.

However, it is clear that these examples are only given to illustrate the invention, other cell types could be used so long as they correspond to the definitions of the invention.

BRIEF DESCRIPTION OF THE DRAWINGS

In these examples reference is made to the following FIGS. 1 to 11:

FIG. 6A represents the immunoprecipitates of the proteins of the invention with L8 MAb from endothelial cells of cornea (1), hepatic epithelial cells (2) and hepatocytes (3), under non-reducing conditions; FIG. 6B shows the same immunoprecipitates under reducing conditions; FIG. 6C represents a two-dimensional electrophoresis showing the pHI of the proteins and FIG. 6D shows an immunoprecipitation after extraction of the proteins with Triton X114, FIG. 8A-8L shows measurements by cytofluorometry on hematopoietic cells, FIGS. 8A to 8L show measurements by cytofluorometry on hematopoietic cells, wherein the windows drawn in the upper panels (A, B, C, G, H, I) indicate the cell population analyzed, the lower panels (D, E, F, J, K, L) show flow cytometric profiles obtained with cells incubated with mAb L8 and middle panels, flow cytometric histograms obtained with control antibody mAb Hep 26.9.

Figure 1A:
FIG. 1 represents micrographs of co-cultures (B,C), or pure cultures (A), of hepatocytes treated (A,C) or not (B) with L8 MAb.

I. REAGENTS AND PRODUCTS USED laminin-entactine complex, laminin, heparansulphate and collagen IV: mouse tumour and sarcoma extracts (Engelbreth-Holm-Swarm) (1) operating according to (2) with the modifications given in (3).

Fibronectin and collagenase: Boehringer Mannheim S. A. Meylan.

Minimal essential medium: Gibco

Medium 199: Gibco

Williams Medium E: (14)

Hybridization probes for the analysis of mRNA: pRSA8 for the albumin gene (4), A4C9 for the aldolase B gene (5) and procollagen $I\alpha_1$ gene (6).

Anti-cytokeratin 18 antibody (anti CK 49) of known specificity (7).

Mouse 3T3 fibroblasts (8).

Endothelial cells of bovine cornea (9).

Epithelial cells of bovine crystallin (10).

Mouse anti-IgM antibody labelled with preoxidase: Nordic Immunological Laboratories, Tilburg, Netherlands.

Mouse anti Ig labelled with fluorescein isothiocyanate: Diagnostic Pasteur, Marnes-la-Coquette, France.

[$^{35}$S]-methionine and [$^{125}$I]Na: Amersham France S. A., Les Ulis.

Anti-mouse goat IgM (Nordic Immunological Laboratories).

Protein A-Sepharose and Ampholines (Pharmacia France S. A., Saint-Quentin-en-Yvelines).

II. Isolation of the cells and culturing isolation of the hepatocytes; preparation of pure cultures or co-cultures.

hepatocytes.

Normal adult hepatocytes are obtained by perfusion of a rat's liver (Sprague-Dawley; 150–200 grams) with a solution of collagenase at 0.025% buffered with 0.1 M Hepes (4-(21-hydroxyethyl)-1-piperazine ethane sulphonic acid) (pH 7.4). The operation is carried out according to the Seglen method described in (11) using the modifications set out by Guguen et al., in (12).

Pure cultures.

In the case of a pure culture, the hepatocytes are seeded in culture flasks in a mixture formed with 75% of MEM medium and 25% of medium 199, supplemented with 10% of foetal calf serum and containing per ml: penicillin (100 IU), streptomycin sulphate (100 $\mu$g), bovine insulin (5 $\mu$g) and bovine serum albumin or BSA (1 mg). The medium, to which $7\times10^{-5}$ M of hydrocortisone hemisuccinate is added, is renewed 4 hours later, then daily.

Co-cultures.

The co-cultures are prepared according to the conditions described in (13).

Briefly, 4 hours after the seeding of the hepatocytes, the medium is removed and non-converted RLEC's, or other cellular types, suspended in a fresh medium, are added. 24 hours later, the medium is supplemented with $7\times10^{-5}$ M of hydrocortisone hemisuccinate and then renewed daily.

To analyze the RNA, the hepatocytes of the co-cultures are selectively separated from the RLEC's by incubation for 10 minutes with a solution of collagenase stripped of calcium (0.05%, pH 7.6) buffered with 0.1 M Hepes.

Cultures of fibroblasts, myofibroblasts and endothelial cells.

Mouse 3T3 fibroblasts, endothelial cells of bovine cornea, human skin fibroblasts and rat's liver myofibroblasts are maintained in a medium supplemented with the serum mentioned above, without insulin, corticosteroids or albumin.

Culture of epithelial cells.

The RLEC cells are isolated by treating 10-day old normal rats' livers with trypsin (14) and (15). Epithelial cells of marmot's liver (MLEC) are prepared from marmots imported from the USA.

The RLEC's, MLEC's and epithelial cells of bovine crystallin are cultured in a Williams E medium supplemented with 10% of foetal calf serum.

III. Production and selection of monoclonal antibodies

Balb/c mice are immunized with a cellular suspension of $10^7$ live RLEC'S. The splenocytes are recovered. Five different fusions are carried out with SP$_2$/O—Ag myeloma cells. The culture supernatants are selected which produce immunoglobulins with regard to the positive response given in the indirect immunofluorescence test with RLEC cells and hepatocytes. From 400 positive hybridoma cultures, about 95% are positive with the RLEC's and the hepatocytes and about 5% are positive only with the RLEC's. Positive clones are then chosen according to their ability to recognize both a liver plasma membrane protein and their inability to react with non-hepatic cells, such as human skin fibroblasts and endothelial cells of bovine cornea. Finally, 24 hybridomas actively secreting antibodies directed against liver plasma membrane proteins are selectively cloned and cultured.

IV. Selection of MAb with regard to the effect on the functional activity of the hepatocytes The ability of the monoclonal antibodies to modify the functional capacities of the hepatocytes in co-culture is checked by adding increasing quantities of culture supernatants of the selected hybridomas to pure cultures of hepatocytes and to co-cultures. 100, 200 and 500 μl of supernatant are added in this way.

The strain is isolated which produces MAb's capable of significantly reducing the survival of the hepatocytes in co-culture but not exerting any effect on the viability of the cells in pure culture. These MAb's are called L8.

As indicated above, this hybridoma strain was deposited under the terms of the Budapest Treaty, at the D.S.M. Mascheroder Weg 1B, D-3300 Braunschweig on 19th Jun. 1991 under the number DSM ACC 2011.

They are characterized as being of IgM class according to Ouchterlony's technique.

Effect on the viability of the hepatocytes and on the secretion of albumin.

The supernatant of cultures of hybridomas secreting L8 MAb is added to co-cultures of hepatocytes and, in a few experiments, IgM L8's concentrated by treatment with euglobulin are used, then ascite fluid is dialyzed against distilled water at pH 5 (see (16) and (17)).

Figure 1B:
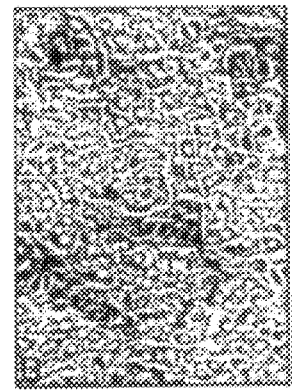
Figure 1C:
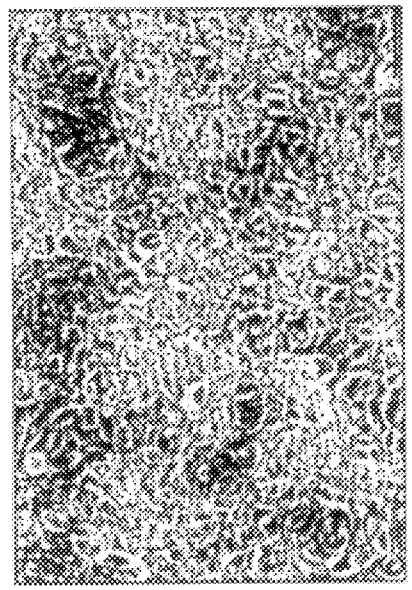

FIG. 1 represents photographs of:
A: 2-day old pure cultures of hepatocytes treated with a supernatant of hybridomas producing L8;
B: 5-day old co-culture of hepatocytes;
C: 5-day old co-cultures of hepatocytes treated with a supernatant of hybridomas producing L8. 500 μl of L8 MAb is added to the culture medium at the start of the culture, then every day at each renewal of the medium.

On the third day, the typical polygonal shape of the hepatocytes maintained in co-culture is lost in the presence of L8 MAb and most of the hepatocytes are dead on the 5th or 6th day, whilst the RLEC's are not affected.

The capacity of the cells to secrete albumin is studied in the cultures treated each day with L8 MAb. The level of secretion of albumin is quantified in the culture media over 5 or 6 days by immunonephelometry by laser operating according to (18).

Figure 2:
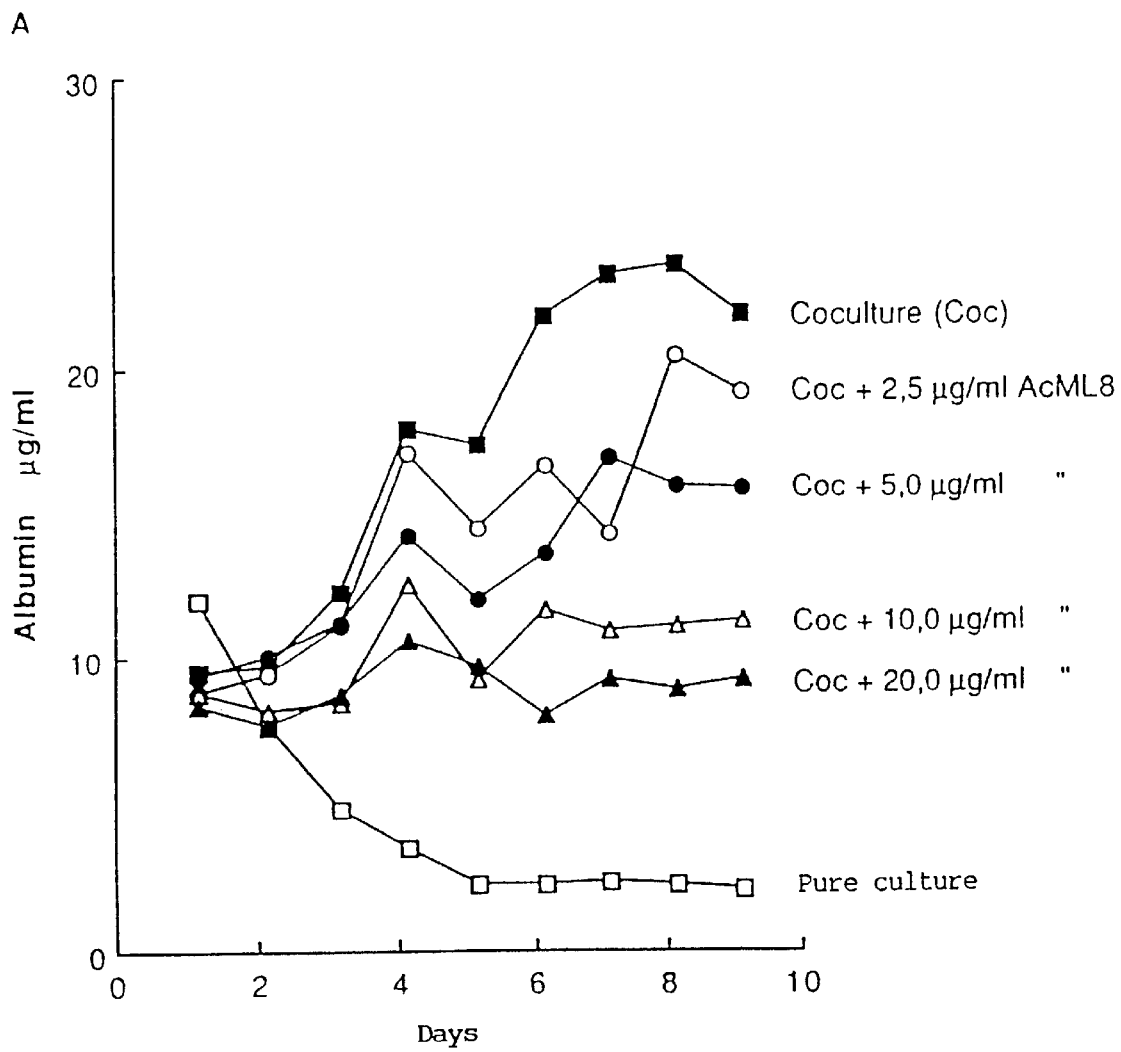
FIG. 2 represents the production of albumin as a function of the duration of the co-culture (in days), in the presence of increasing quantities of L8 MAb.

The MAb is added at different concentrations. The level of serum albumin is measured in the medium removed each day. The results obtained with the pure cultures (--), the control co-cultures (-■-) maintained without addition of L8 MAb, and co-cultures to which 2.5 (-○-), 5 (-●-), 10 (-Δ-) and 20 μg/ml (-▼-) of partially purified MAb are added, are represented on FIG. 2. The antibody is added during the seeding of RLEC and every day at each renewal of the medium.

It is noted that the secretion of albumin is maintained at a high level in the non-treated co-cultures and falls in those to which 10 or 20 μg of partially purified antibody per ml of medium has been added (FIG. 2a).

Class of L8 MAb:

The L8 MAb is characterized as being of IgM class according to Ouchterlony's technique.

Two experiments are set out hereafter carried out to determine at what moment the L8 MAb exerts an effect on the hepatocytes in co-culture.

In a first experiment, the L8 MAb is added at the start of cellular seeding, then the treatment is stopped 1, 2, 3 or 4 days later.

In a second series of experiments, the co-culture is initiated without antibody and the treatment is started only 1, 2 or 3 days later.

The effect of the L8 MAb is evaluated by measuring the capacity of the hepatocytes to survive and to secrete albumin in the medium.

It is noted that the suppression of the treatment with L8 MAb on the first day as well as the late addition of antibody on the third day has no significant effect on the cellular viability and the production of albumin. An inhibiting effect is revealed only when the antibody is present between the first and second day after the seeding of the RLEC's corresponding to the establishment of contacts between the two cell populations. The first day of phase shift represents the time necessary for the attachment of the RLEC's, their growth and the obtaining of a confluence with the hepatocyte colonies.

The study by microcinematography of the liver epithelial cells establishing contacts with hepatocytes shows the appearance of a clear and flat zone at the contact site after 20 minutes and a reorientation of the intracytoplasmic organelles radially in the direction of this site.

V. Immunolocalization of the protein reacting with the L8 MAb

The pure cultures of hepatocytes and the co-cultures are fixed in a 4% solution of paraformaldehyde buffered with 0.1 M sodium cacodylate (pH 7.4) for 30 minutes at 4° C. The MAb's are localized using indirect staining with immuno-peroxidase or the indirect immunofluorescence technique. The incubations are carried out in the presence of 0.1 or 0.2% of saponin. A second antibody is constituted by a mouse anti-IgM antibody labelled with peroxidase or by an anti-mouse immunoglobulin labelled with fluorescein isothiocyanate.

The immunopositive reaction with the L8 MAb is uniformly localized at the level of the plasma membrane of freshly isolated hepatocytes and of pure cultures of hepatocytes and is localized only in the first 4 days then disappears.

By contrast, the L8 MAb immunoreacts with the plasma membranes of hepatocytes in co-culture for two weeks. The reaction then slowly decreases over time.

Figure 3A:
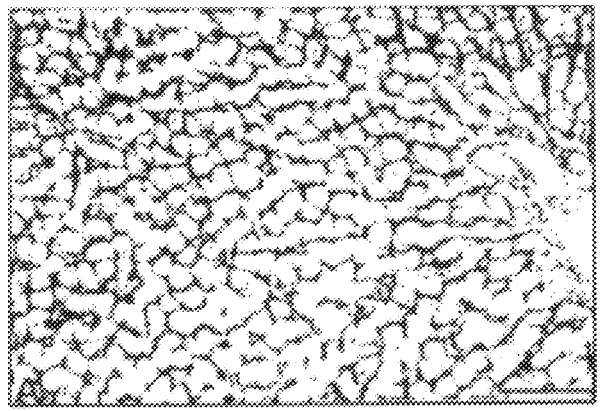
FIG. 3A is an immunolocalization on a section of adult rat's liver and FIGS. 3B and 3C are micrographs showing the immunolocalization of the L8 MAb-protein complex in cultures of hepatocytes, FIG. 4 gives the results of the hybridization of mRNA of the hepatocytes with different probes.
Figure 3B:
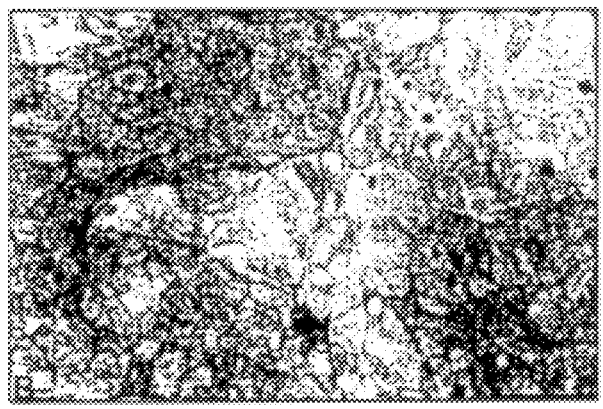

FIG. 3B) represents a photograph of a 3-day old co-culture showing, using the immunofluorescence technique, the localization of the protein on the plasma membrane and its uniform distribution around the cells. It seems to be expressed strongly by the hepatocytes and weakly by the RLEC'S.

For the study by electron microscopy, the cells are then fixed with 2.5% of glutaraldehyde, then incubated for 30 minutes with a solution containing 1% of osmium in a 0.1 M buffer of cacodylate. The cells are then dehydrated in pure ethanol and imbedded in Epon$^R$.

Figure 3C:
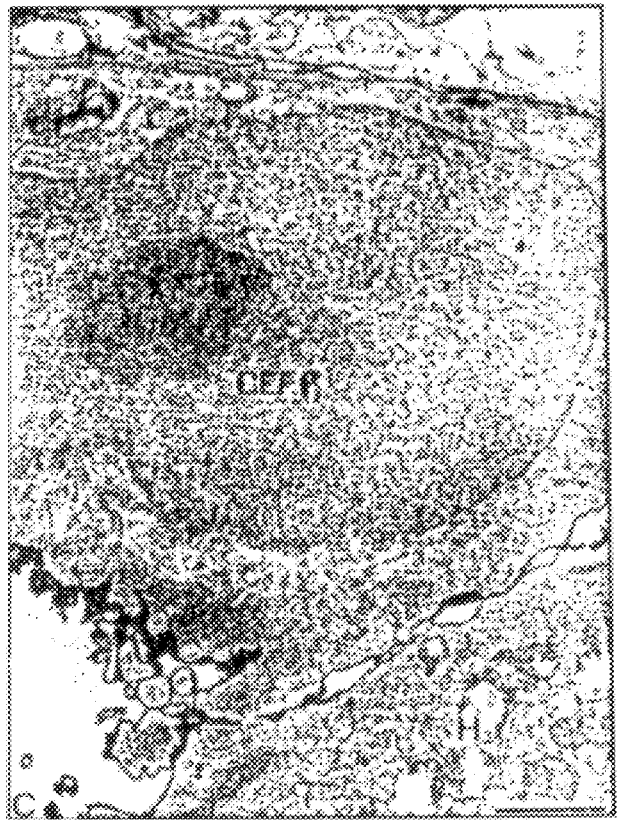

FIG. 3C shows a micrograph taken with an electron microscope of a 3-day old co-culture. The protein molecule is detected by the reaction of immunoperoxidase. Dense electron deposits are observed, uniformly distributed on the cellular surface of the hepatocytes and the RLEC's. No intracellular staining is visible.

FIG. 3A shows the distribution of the protein on a section of the liver of an adult rat. It appears to be uniformly distributed in the lobule and mainly localized at the sinusoidal pole of the cells.

VI Reaction of different cell types with rat hepatocytes in co-culture and immunoreactivity with the L8 MAb The results obtained with co-cultures of different cell types with rat hepatocytes are given hereafter. It is considered that the cells which are capable of improving both the survival of the cells and the albumin secretion are capable of establishing cellular interactions with the hepatocytes. The immunoreactivity with the L8 MAb is revealed by indirect localization with immunoperoxidase. The results are given in Table 1 below.

TABLE 1

| Cells | Species | Reactivity with L8 MAb | Cellular interaction |
|---|---|---|---|
| Epithelial cells of |  |  |  |
| liver RLEC (SDIII) | Rat | + | + |
| - liver (SDVI) | Rat | + | + |
| - liver MLEC | Marmot | + | + |
| - crystallin | Bovine | − | ND* |
| Other cell types |  |  |  |
| - Liver myofibroblasts | Rat | − | ND |
| - Skin fibroblasts | Human | − | ND |
| - Cornea endothelial cells | Bovine | − | ND |
| - 3T3 fibroblasts | Mouse | + | ND |

*ND indicates that no reactivity was detected.

Examination of this table shows that two different RLEC cell lines and one epithelial cell line of marmot liver (MLEC) are capable of improving the survival of rat hepatocytes and the secretion of albumin. All these cells are immunoreactive with L8 MAb. On the other hand the epithelial cells of bovine crystallin and the rat's liver myofibroblasts do not react with the hepatocytes in co-culture.

Furthermore, tests were carried out combining hepatocytes of different species with the RLEC's. The hepatocytes of a mouse, marmot, dog, baboon and man are all capable of reacting with the RLEC's and of maintaining a high functional stability in co-culture.

All of these results show that the cells which give rise to a reaction of antigen-antibody type with the L8 MAb are capable of reacting with the hepatocytes in coculture, giving rise to the establishment of intercellular communications which allow the differentiated state of the hepatocytes to be maintained.

VII. Study of the action of the L8 MAb on the expression of liver-specific genes of hepatocytes in co-culture The levels of mRNA of albumin (a), procollagen $I\alpha_1$ (b) and aldolase B (c) of freshly isolated hepatocytes (0) and of hepatocytes maintained in 2- or 5-day old co-cultures with (+) or without (−) 20 $\mu$g/ml of partially purified L8 MAb are analyzed. By way of comparison the pure cultures were analyzed after 2, 4 and 6 days.

A corresponds to the co-cultures, B to the pure cultures of hepatocytes, 2, 4 and 6 days after seeding.

Equal quantities of total RNA (20 $\mu$g) from these different sources are used.

The total RNA is obtained according to the technique of Chirgwin et al. (19) with 5 M of guanidinium thiocyanate/CsCl.

The total RNA (20 $\mu$g) is dissolved by electrophoresis and transferred onto a nitrocellulose filter. The filter is prehybridized in a standard manner and hybridized with a nick-translated DNA probe $3\times10^6$ cpm/ml of $^{32}$P for 18 hours at 65° C.

Figure 4A:
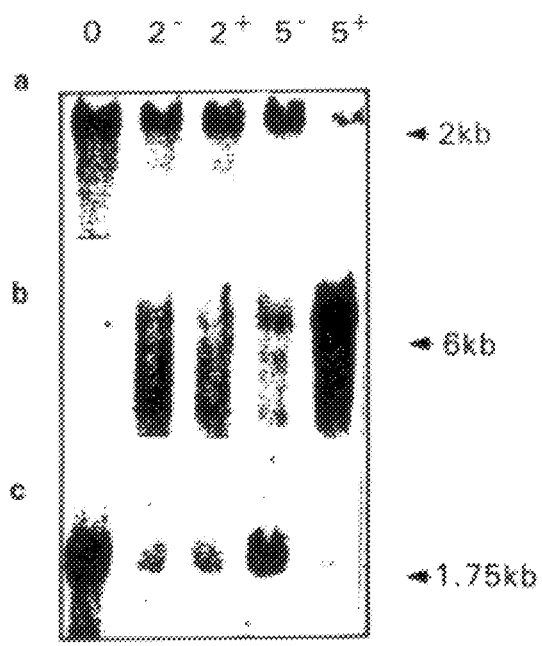
FIGS. 4A and 4B represent the immunoblots obtained when hybridizing with CDNA probes (A) and (B) respectively, with mRNA of albumin (a), procollagen $I\alpha_1$ (b) and aldolase B (c) of freshly isolated hepatocytes (O) and of hepatocytes maintained in 2 or 5 day old co-cultures with (+) or without (-) partially purified L8 mAb.
Figure 4B:
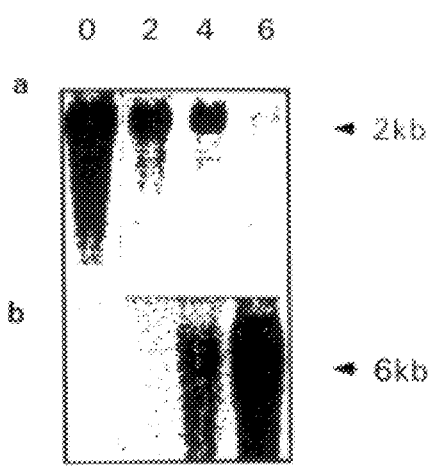

The hybridization is carried out with an excess of cDNA probes corresponding to (A), (B) and (C). The results are given in FIG. 4. The levels of mRNA of the albumin and the aldolase B increase greatly from the second to the fifth day in the non-treated co-cultures whilst these levels decrease greatly in the presence of L8 MAb on the fifth day. On the other hand, increasing quantities of procollagen $I\alpha_1$ are observed in the presence of the L8 MAb.

In order to demonstrate that the L8 MAb specifically alters the regulation of the liver-specific genes, mediated by the cell-cell contact, pure cultures of hepatocytes are extended to eight days in the presence of 25 mM of nicotinamide and continuously exposed to L8 MAb. Neither the morphology nor the secretion of albumin is modified in these cells when L8 MAb is present. On the other hand, the co-cultures with or without nicotinamide lose their capacity to secrete high levels of albumin in the presence of L8 MAb.

In order to verify that the L8 MAb has no direct effect on the pure hepatocyte cultures, the products of translation in vitro of the hepatocytes non-treated or treated daily with L8 MAb and maintained in pure culture or in co-culture were analyzed. To this end, 5 $\mu$g of total RNA from pure cultures and co-cultures, nontreated or treated daily with 10 $\mu$g/ml of partially purified L8 MAb (1-, 3- and 5-day old) are translated in vitro using rabbit reticulocyte lysates (20) containing 50 $\mu$Ci of [$^{35}$S]-methionine. The translation is carried out for 2 hours at 30° C. The substance precipitable with trichloracetic acid ($4\times10^5$ cpm) is developed on SDS-PAGE and autoradiographed. It is noted that the profile of the proteins synthesized by the pure cultures is similar during the culture period, whether or not L8 MAb is present. On the other hand, the treatment of the co-cultures with L8 MAb for 3 days specifically brings about important changes in the level of synthesis of the different proteins.

VIII. Study of the effect of L8 MAb on the organization of the cytoskeleton of hepatocytes and on the deposition of the components of the extracellular matrix Cytoskeleton It has already been established that the cellular shape and the cytoskeleton are closely associated with the differentiated phenotype of hepatocytes. The examination carried out focused on the cell-cell contacts with RLEC's in order to verify whether they bring about early or late changes in the cytoskeleton. CK8 and CK18 cytokeratins, which form the intermediate-sized filaments of the cytoskeleton of hepatocytes, were analyzed. The immuno-localization of the CK18 protein is carried out in pure cultures and in co-cultures in the presence or in the absence of L8 MAb. The cytokeratin filaments form a complex network uniformly distributed in the cytoplasm of hepatocytes in pure cultures whilst they are mainly localized on the cell periphery just below the plasma membrane in co-culture. It was noted that the daily addition of L8 MAb from the start of the co-culture greatly disturbs the reorganization of these components of the cytoskeleton.

Deposition of the extracellular matrix

The staining of the reticulin by impregnation with silver of the extracellular matrix is carried out according to the method of Gordon et al. described in (20) in co-cultures fixed with a mixture of 4% paraformaldehyde and 2.5% glutaraldehyde in a cacodylate buffer (pH 7.4) for 15 minutes at 4° C.

Figure 5A:
FIG. 5 represents the micrographs of co-cultures with the deposition of matrix fibres, treated (B,D) or not (A,C) with L8 MAb, then stained with reticulin (silver impregnation).
Figure 5B:

It has already been demonstrated that the presence of the extracellular matrix is associated with the maintenance of the hepatocyte function in co-culture. The role of the L8 MAb on the deposition of the extracellular matrix was studied in co-culture using the staining of the reticulin. The micrographs obtained with co-cultures established by adding the RLEC's 4 hours after having seeded the hepatocytes to obtain a single layer of cells are given in FIGS. 5A and 5B.

The staining is carried out on 3-day old co-cultures, treated daily with 2 µl/ml of ascite fluid of $SP_2/O$—Ag myeloma cells acting as control (A) and ascite fluid obtained with hybridomas secreting L8 MAb (B).

In the non-treated cells in co-culture, the extracellular matrix is first of all localized between the two cell populations. This frame or network gradually covers the hepatocyte colonies in a week. The early and daily addition of 5 µg and 10 µg per ml of L8 MAb to the co-cultures greatly inhibits the deposition of the extracellular matrix under the two co-culture conditions used.

As the results given above showed that the activity of the protein of the invention is inhibited by the monoclonal antibody specifically recognizing it during the establishment of contacts between the two cell populations, experiments were carried out to study the effect of this antibody on the attachment of the hepatocytes to the RLEC'S.

Figure 5C:
Figure 5D:
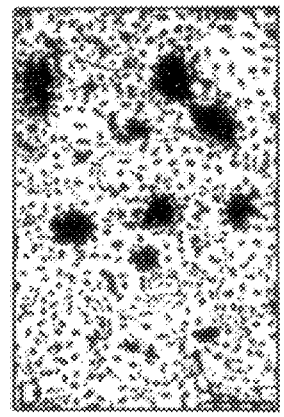

The micrographs obtained with these co-cultures are given in FIGS. 5C and 5D.

3.5 cm diameter dishes covered with a confluent single layer of RLEC are preincubated with 2 µl of ascite fluid of $SP_2/O$—Ag (C) or of L8 (D) per ml of medium without serum for one hour. The freshly isolated hepatocytes ($10^6$ cells) are then seeded and maintained at 37° C. in the same medium containing $SP_2/O$—Ag or L8 MAb. The media of the flasks are collected in duplicate after 2, 3, 4, 7 and 22 hours and the number of unattached hepatocytes is estimated by measuring the lactate dehydrogenase activity after lysis of the cells with PBS containing 0.2% of Triton X-100.

No significant difference is observed in the attachment of the hepatocytes to the RLEC's in the presence of L8 MAb. The differences between the treated or non-treated cells are observed only after three days and consist of a delay in the spread of the hepatocyte in the co-culture with L8 MAb, whilst the non-treated cells do not spread well. Furthermore, the deposition of the extracellular matrix is greatly reduced and the viability of the hepatocytes is limited to a few days as indicated above.

It was also verified whether the L8 MAb is capable of altering the adhesion of the hepatocytes to different components of the extracellular matrix.

The results obtained with the following substrates: EHS gel, fibronectin, collagen IV, laminin, lamininentactine complex, heparan-sulphate, are examined. The deposits at the bottom of the tissue culture flasks containing 0.32 cm² wells containing 100 µl of medium without serum are recovered with 2 µg of proteins. After 2 hours, 3% of BSA at a final concentration of 1.5% is added and left for another 30 minutes. The medium is discarded and the hepatocytes previously incubated for 30 minutes in a medium without serum containing increasing quantities of L8 MAb or $SP_2/$O—Ag ascite fluid and 0.02% of BSA are seeded. After one hour, the cultures are washed twice with PBS. The number of attached and non-attached hepatocytes is measured as described above.

The seeding of the hepatocytes in a medium containing increasing concentrations of L8 MAb or of $SP_2/O$—Ag ascite fluid does not prevent or delay the attachment to substrates of plastic, fibronectin, laminin, lamininentactine-collagen IV complex, heparan-sulphate-proteoglycan. The pre-incubation of the cells with L8 MAb does not affect these results.

It was also verified that the hepatocytes seeded with L8 MAb on dishes covered with ESH gel show no change in their survival and their functional capacity.

These data suggest that the epitope recognized by L8 MAb is probably not involved in the reactivity with the extra-cellular matrix.

IX. Characterization of the polypeptides recognized by the L8 MAb

The immunoprecipitation on cell lysates after iodination of the cell surface of the hepatocytes and RLEC's is carried out (21). The cells are labelled with Na [$^{125}$I] by catalytic reaction with lactoperoxidase. The lysates of the different sources are precipitated with ascite fluid obtained with hybridomas secreting L8 MAb. An incubation is carried out for 90 minutes with 3 µl of ascite fluid. In order to eliminate the non-specific fixations, the ascite fluid is treated with protein A-Sepharose before use. The samples are then incubated with IgM made in goat anti-mouse, then protein A-Sepharose. The affinity spheres are washed with the lysis buffer and the substance fixed is eluted with 100 µl of buffer sample according to Laemmli (22) in order to determine the molecular weight, or with 100 µl of lysis buffer according to O'Farell (23) in order to determine the pI. SDS-PAGE electrophoresis is carried out in poly-acrylamide gel forming a linear gradient of 4 to 15% or of 7.5 to 15% in the Laemmli buffer system mentioned above.

The measurement of the iso-electrofocus is carried out with Ampholines of pH 3 to 10 in the O'Farell buffer system mentioned above.

determination of the molecular weight.

FIG. 6A gives the results obtained by SDS-PAGE analysis under reducing conditions with immunoprecipitates of lysates of endothelial cells of bovine cornea (track 1), hepatocytes (track 2) and RLEC (track 3).

The SDS-PAGE analysis of the immunoprecipitates of L8 MAb shows two peptide chains having apparent molecular weights of 85 kD and 73 kD both for the hepatocytes and the RLEC's. These two bands are never detected after immunoprecipitation with the ascite fluid of the $SP_2$-O—Ag myeloma cells used for the fusion and acting as control, or when iodated detergent lysates are prepared from endothelial cells of bovine cornea (track 1).

The results of the SDS-PAGE analysis under non-reducing conditions of the immunoprecipitates obtained with the hepatocytes (track 1) and the RLEC's (track 2) are represented in FIG. 6B.

It is noted that the two polypeptides are constantly present both under the reducing conditions and the non-reducing conditions, which suggests that the two chains are not linked by disulphide bridges. The heaviest chain (85 kD) appears to migrate slightly more quickly under non-reducing conditions with an apparent molecular weight of 80 kD.

measurement of the pI (FIG. 6C)

The pI is about 4.9 to 5.1 for the polypeptide of 85 kD and 5.2 for that of 73 kD.

The hepatocytes are subjected to an extraction with Triton X-114 and to a phase operation at 30° C. as described in (24). The results obtained are shown in FIG. 6D. The two polypeptides are essentially recovered from the hydrophobic phase (track 1), which is to be connected with their membrane character. They cannot be extracted from the plasma membrane after treatment with PBS or EDTA. The aqueous phase (track 2), the hydrophobic phase (track 3) and the aqueous phase (track 4) are immunoprecipitated with L8 MAb.

X. Study of the immunoreactivity of different tissues with L8 MAb

Ovarian follicle of a rat

Figure 7A:
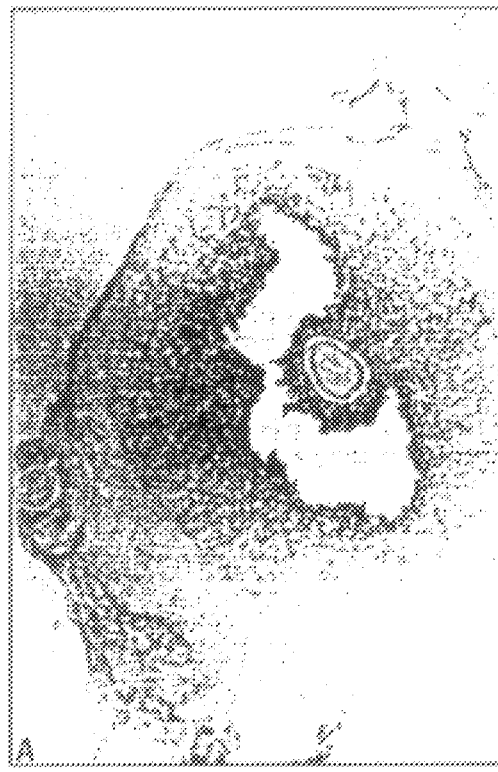
FIG. 7 shows sections of adult rat tissues, after reaction with L8 MAb, A/ and B/ of ovarian follicle, C/ of the small intestine, D/ of seminiferous tubules.
Figure 7B:
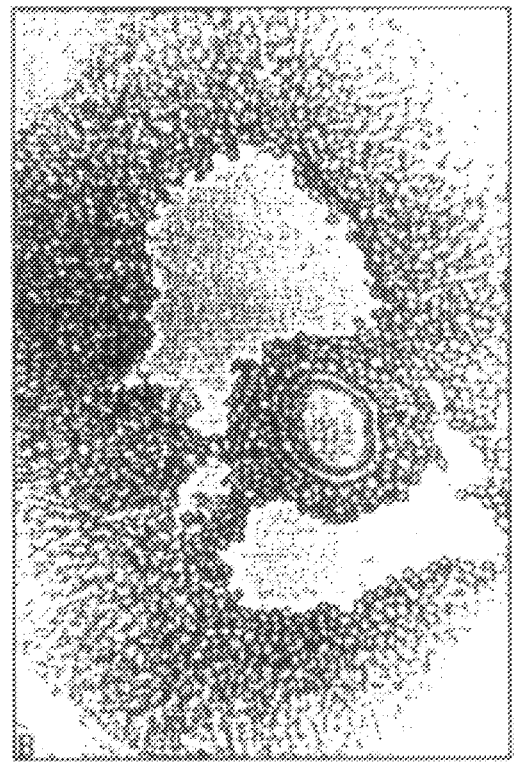

Photographs of the ovarian follicle of a rat, weak (A) and strong (B) respectively after reaction with L8 MAb are shown in FIGS. 7A and 7B.

The mature follicle can be observed in these figures containing follicular cells and the ovocyte with formation of an atrium.

A small immature follicle without an atrium can also be observed.

Labelling all around the follicular cells near to the ovocyte and around the ovocyte itself is noted, indicating an immunoreaction with L8 MAb.

Small intestine

Figure 7C:
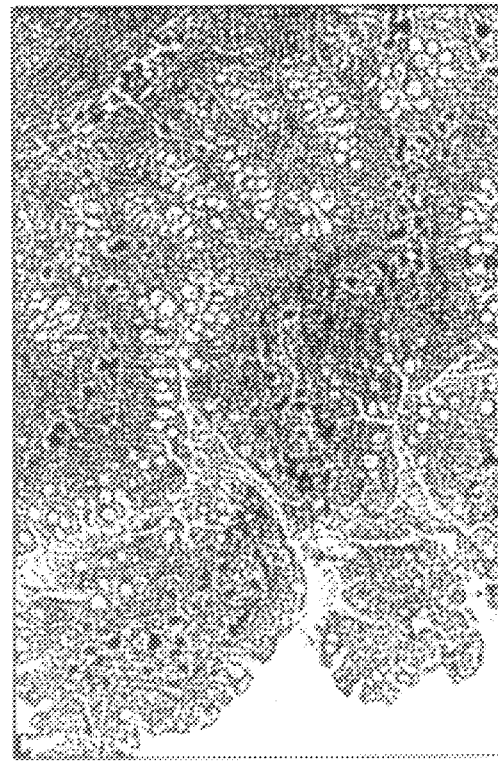

A photograph of a section of the small intestine showing intestinal villi is given in FIG. 7C. No reaction with L8 MAb is observed. Only the red blood corpuscles appear stained.

Rat's testicle

Figure 7D:
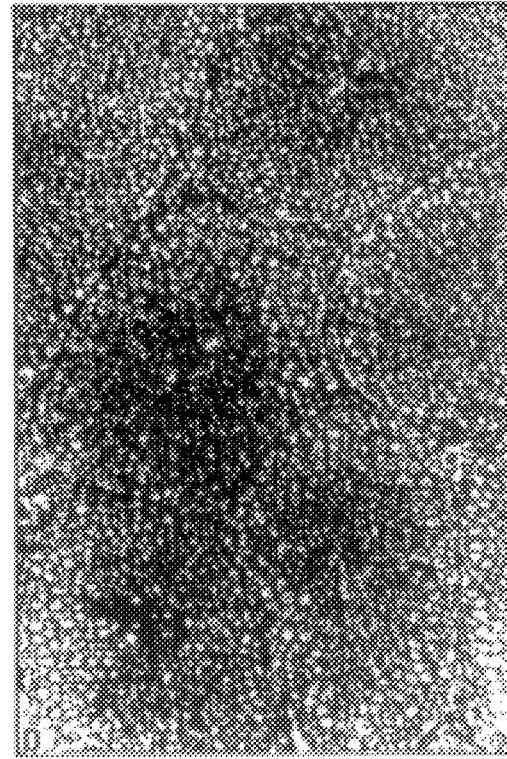
Figure 8A:
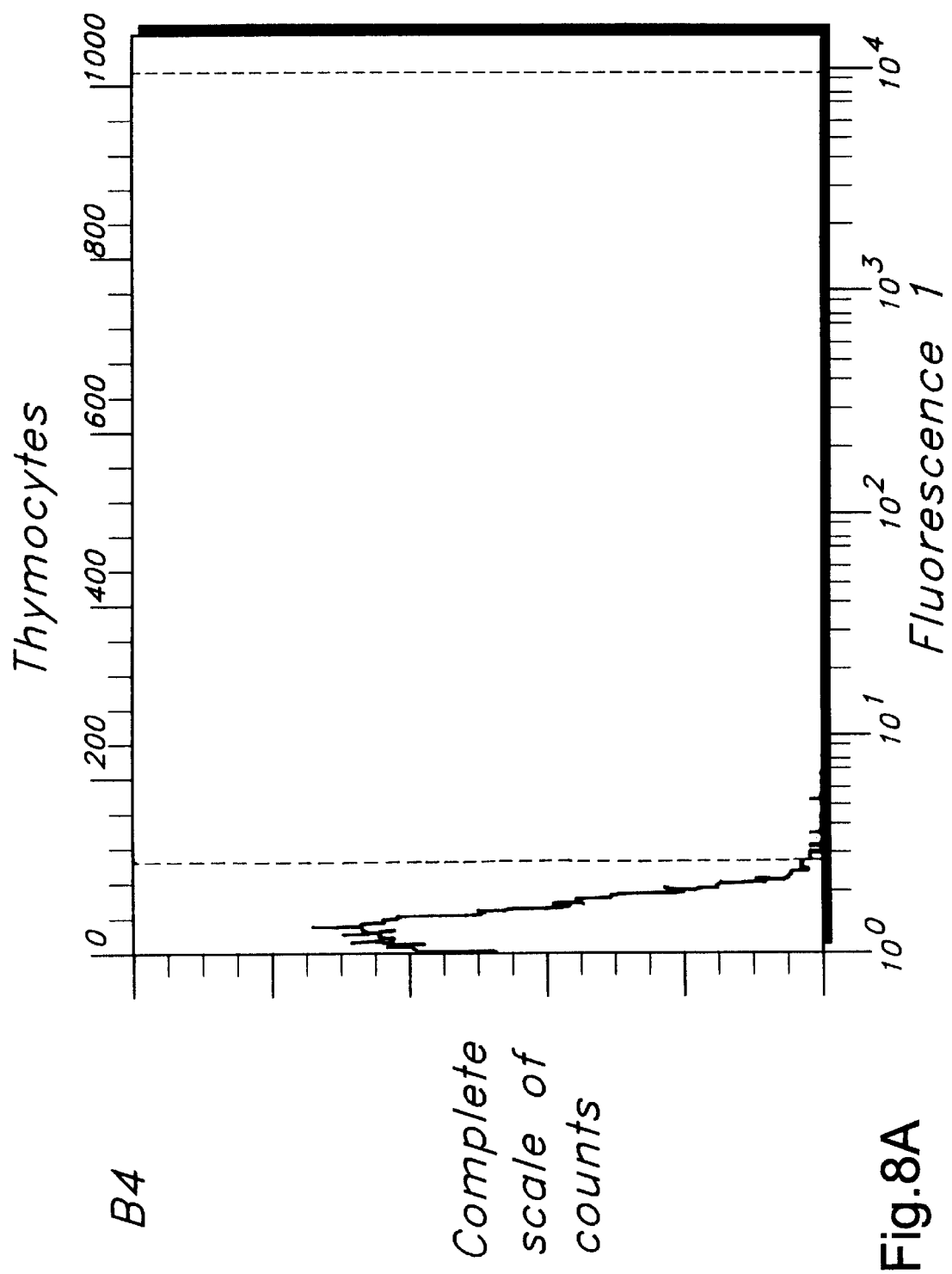
Figure 8B:
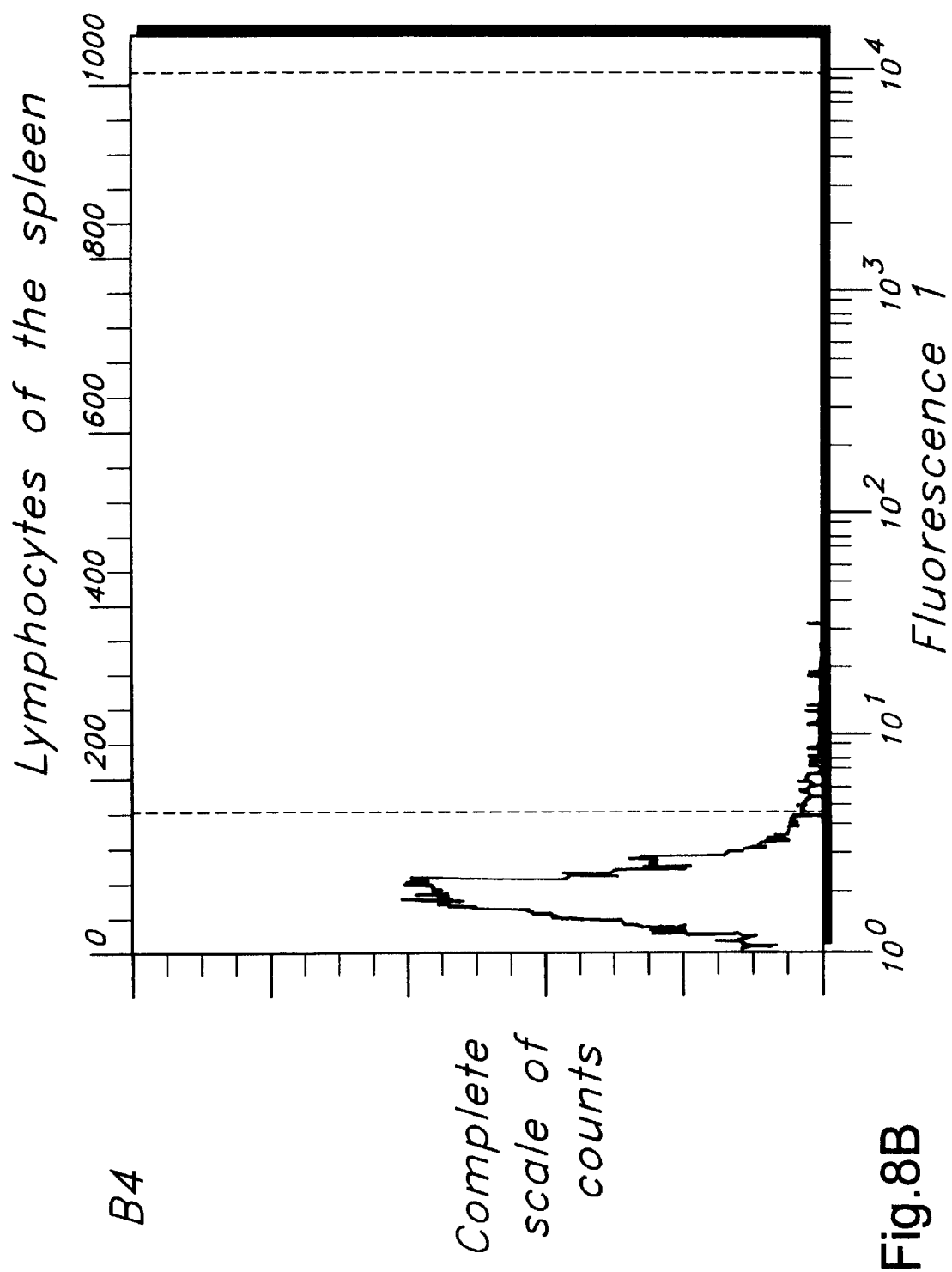
Figure 8D:
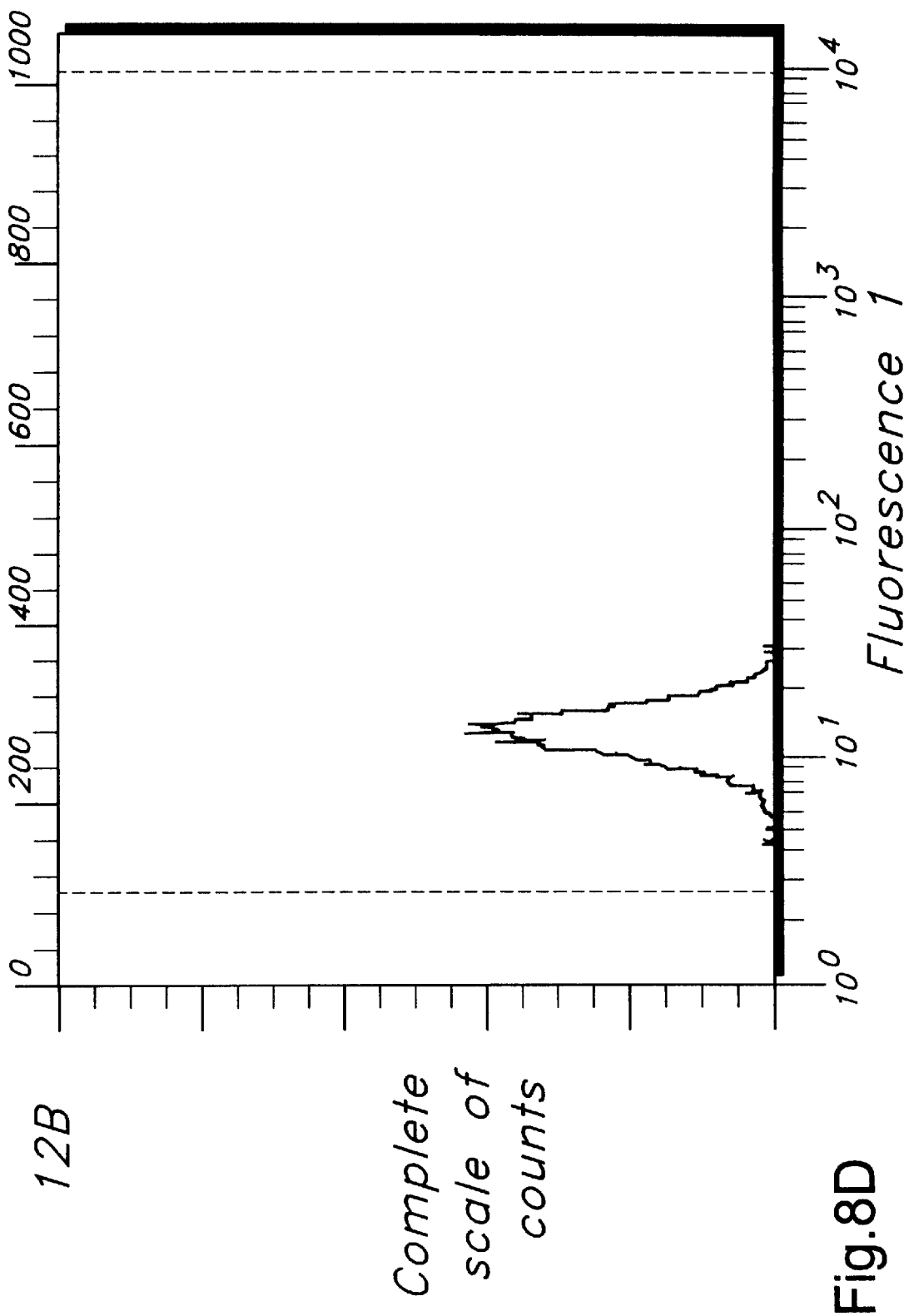
Figure 8E:
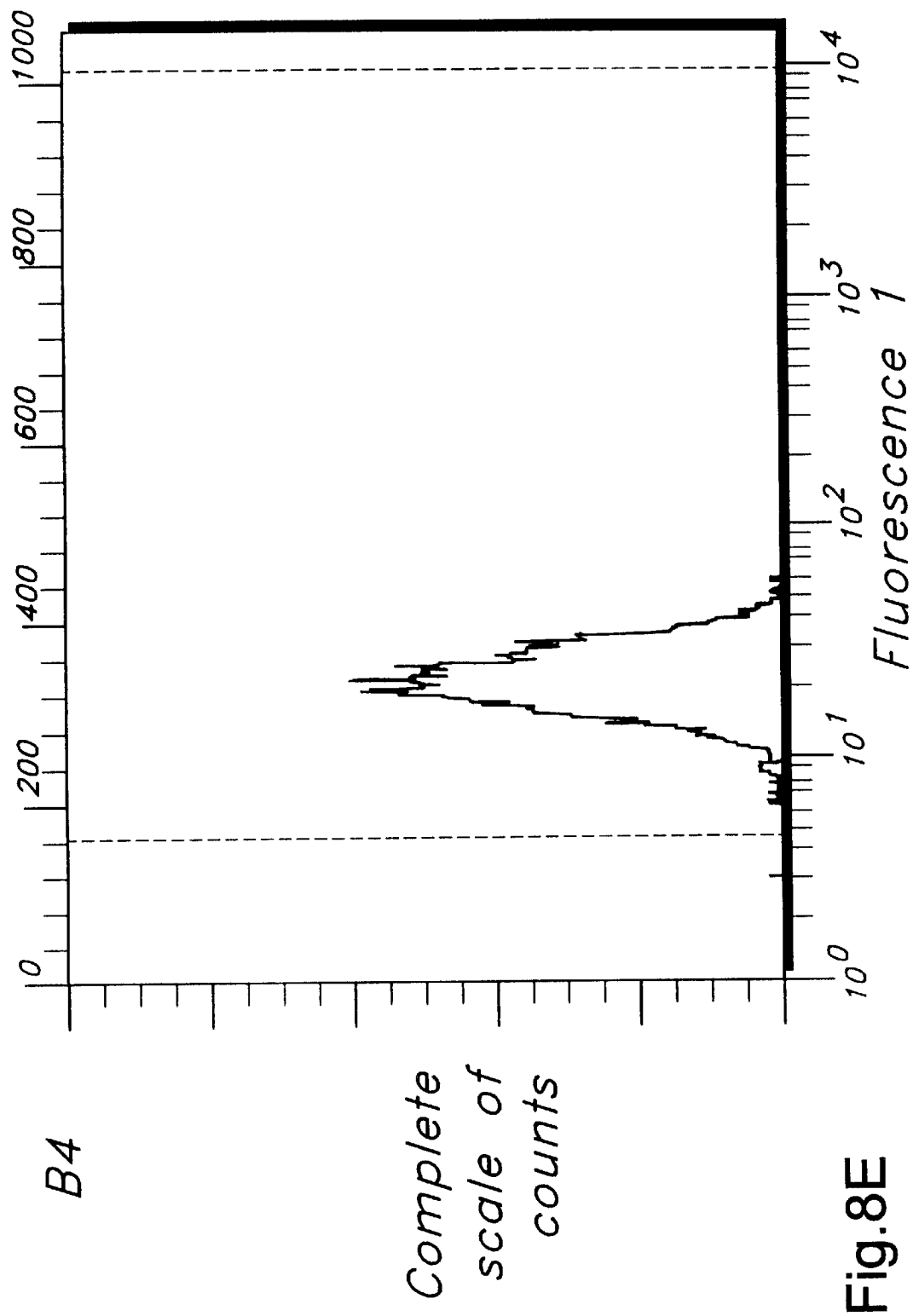
Figure 8F:
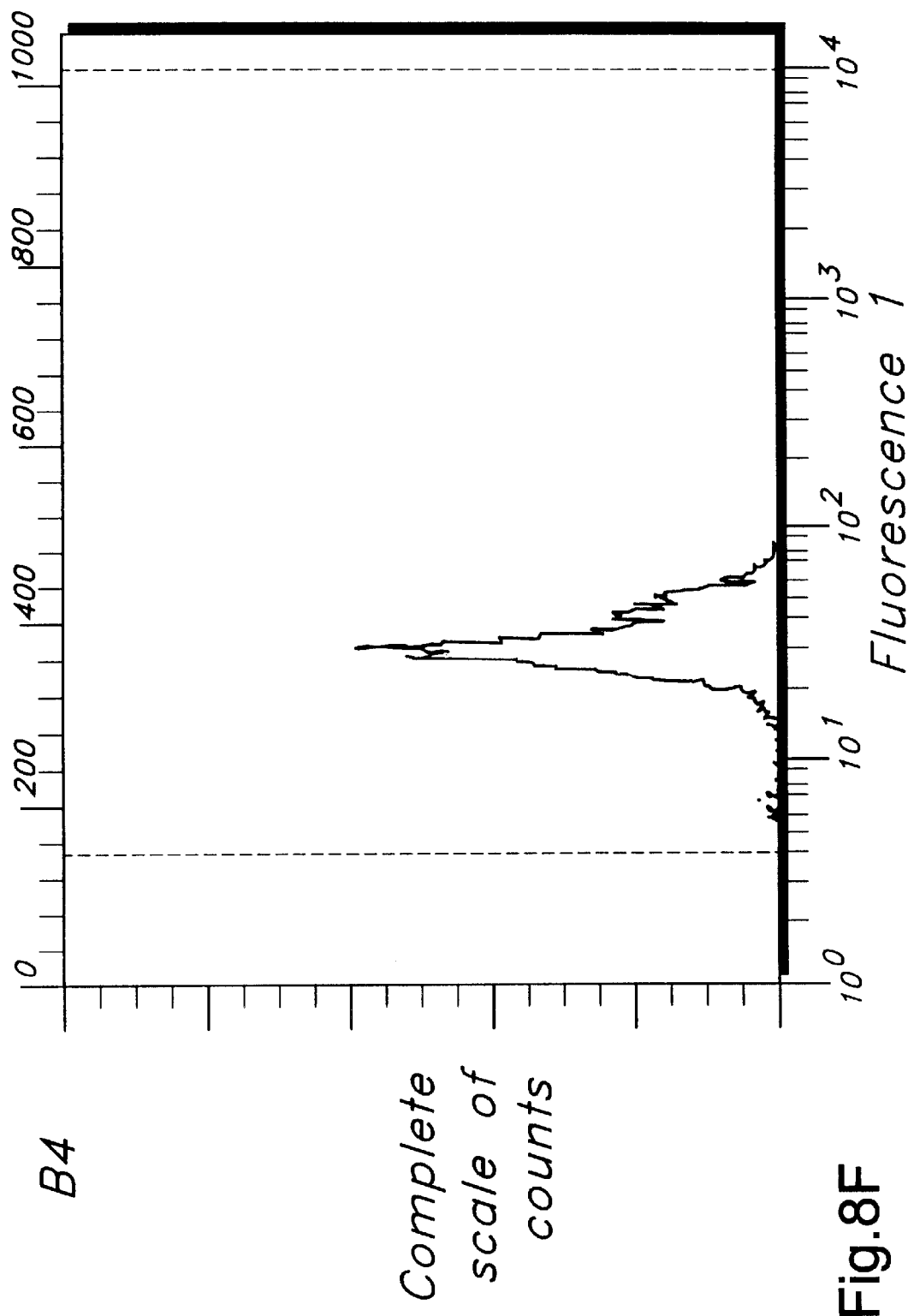
Figure 8G:
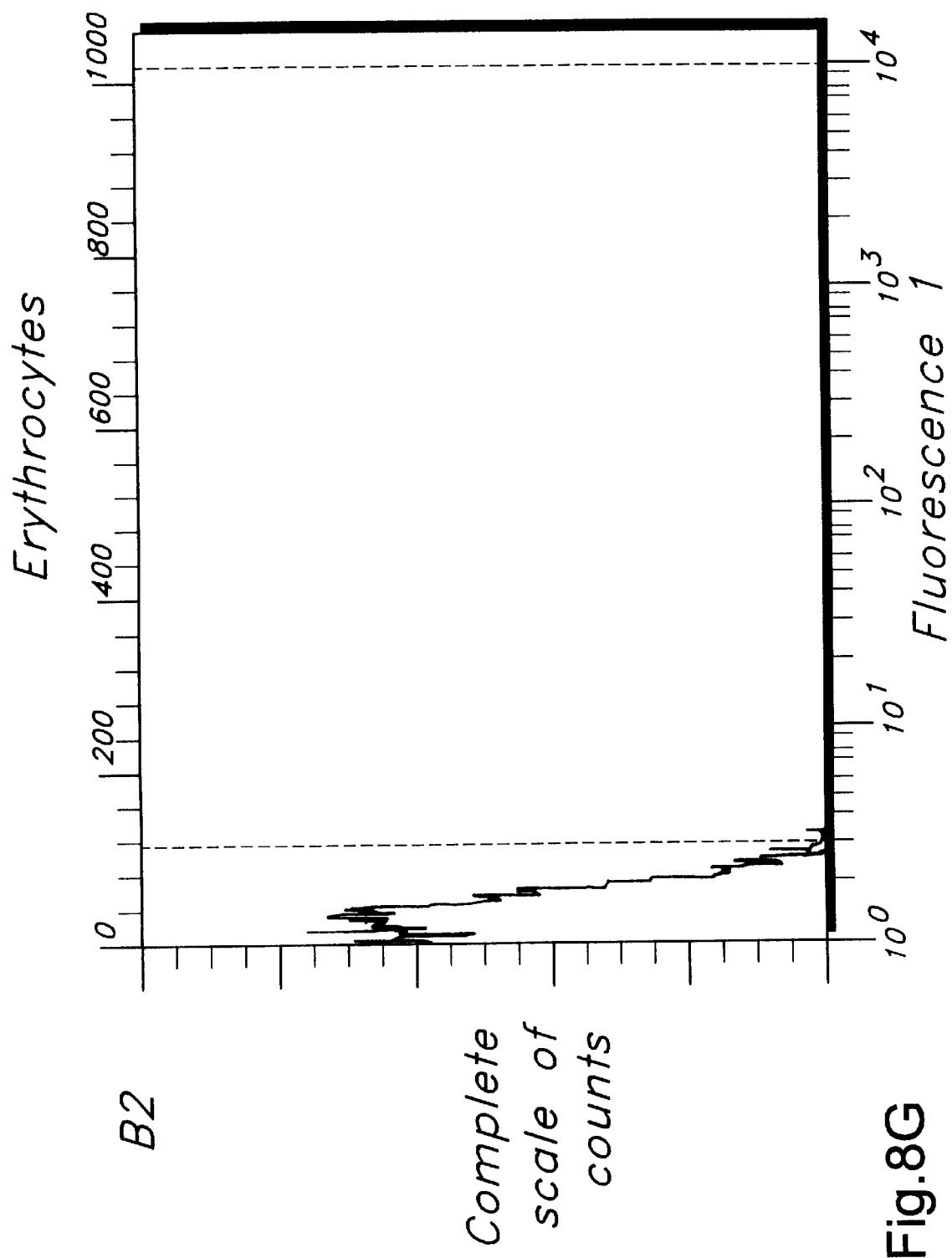
Figure 8H:
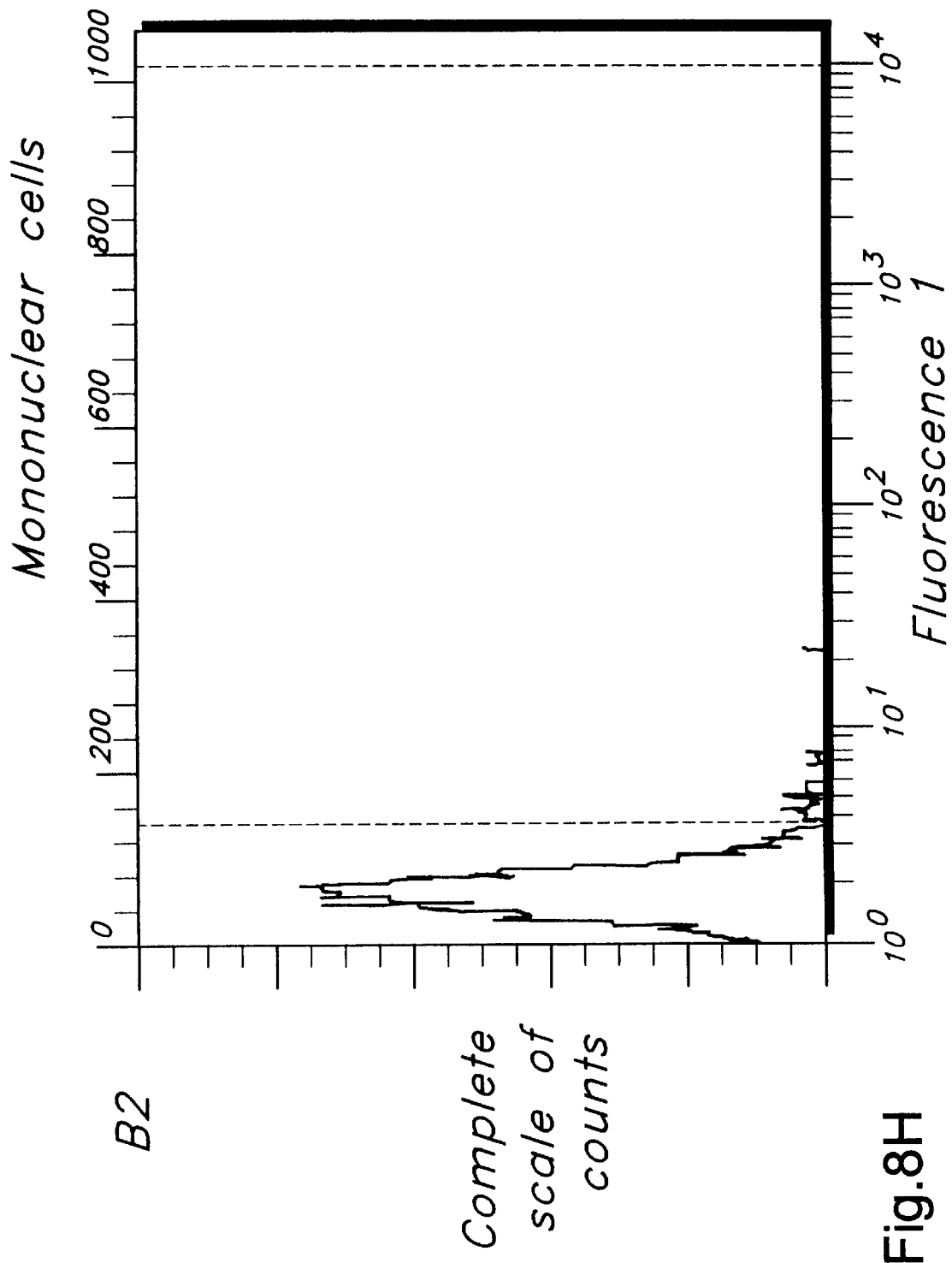
Figure 8I:
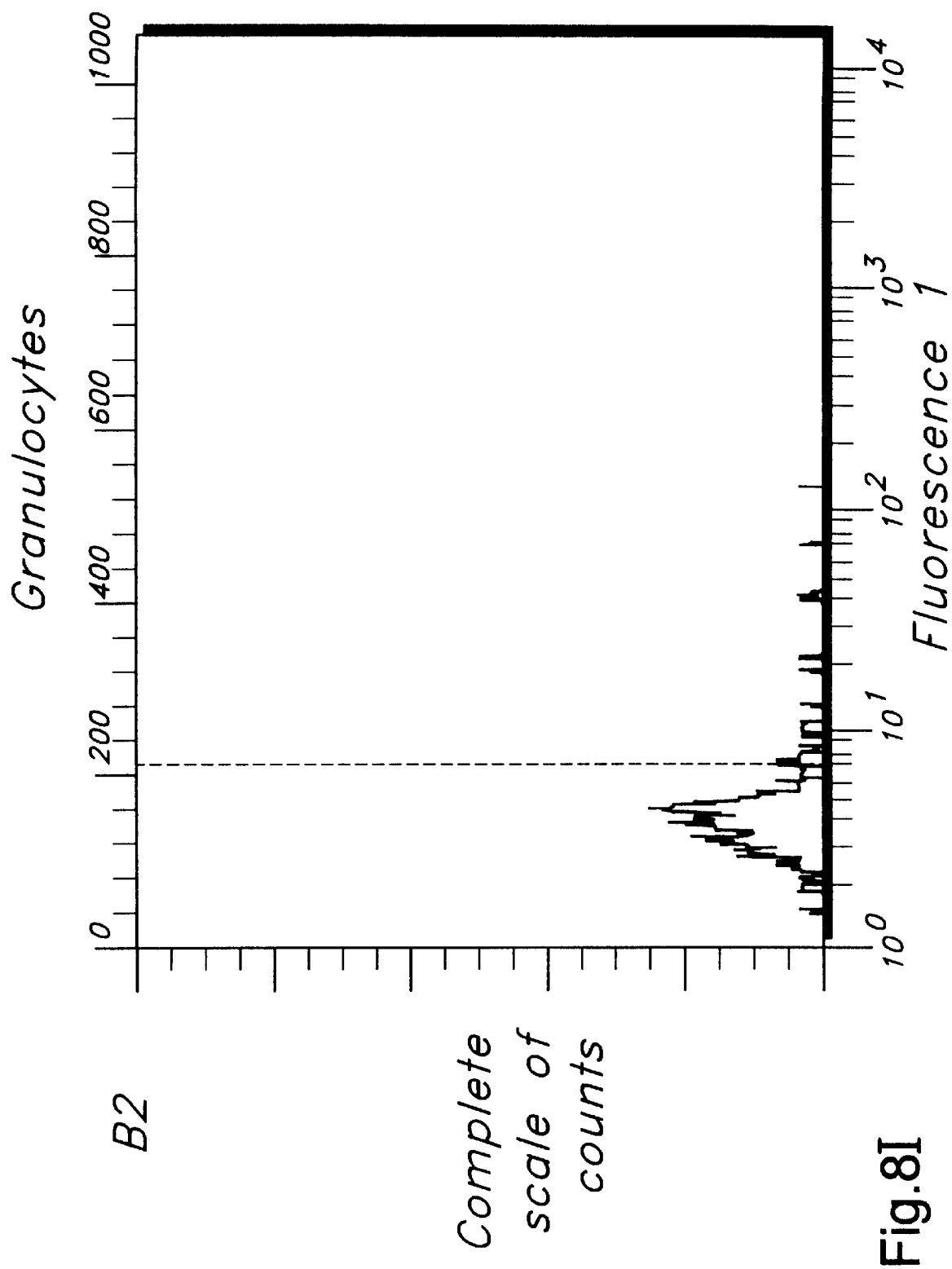
Figure 8J:
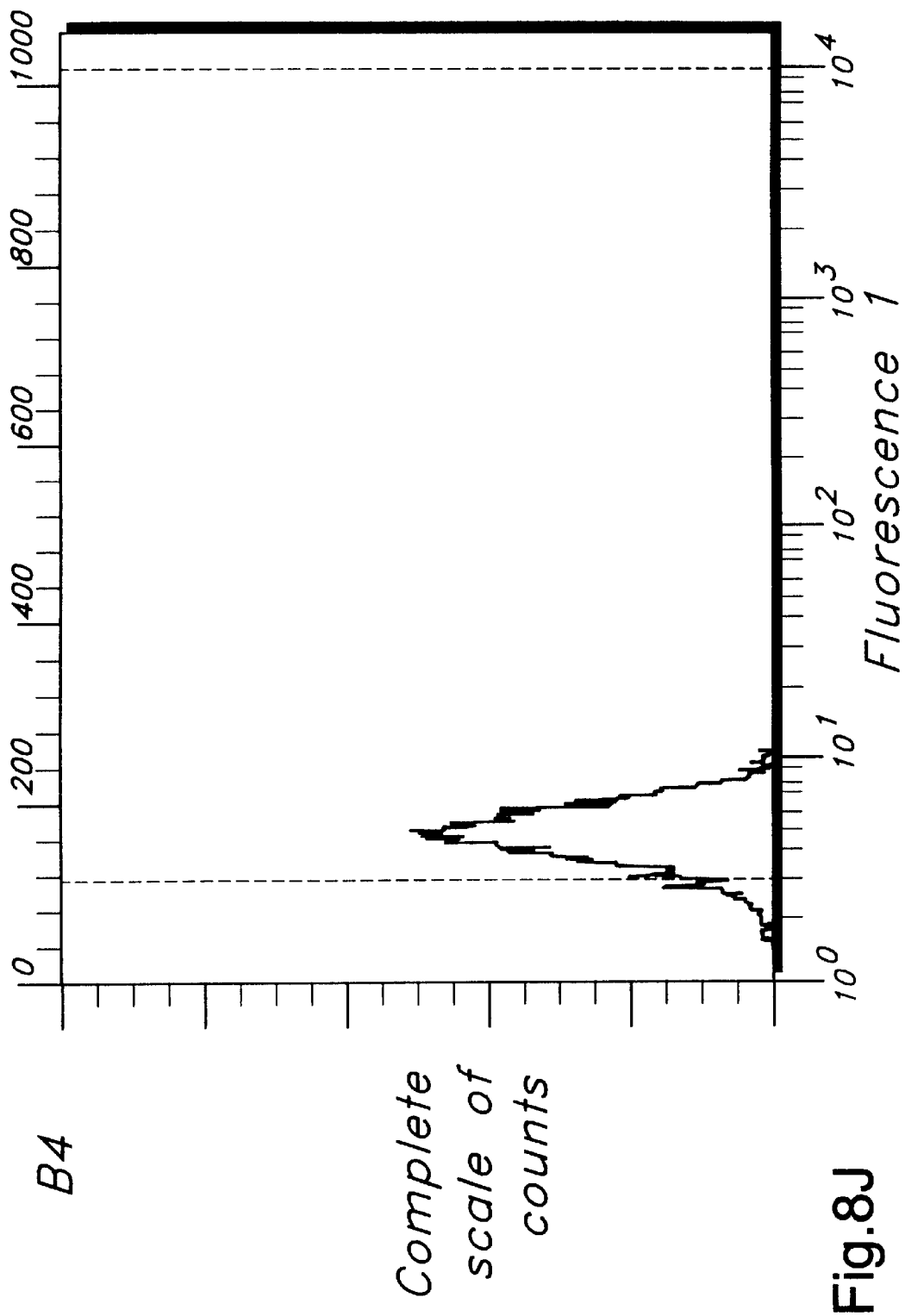
Figure 8K:
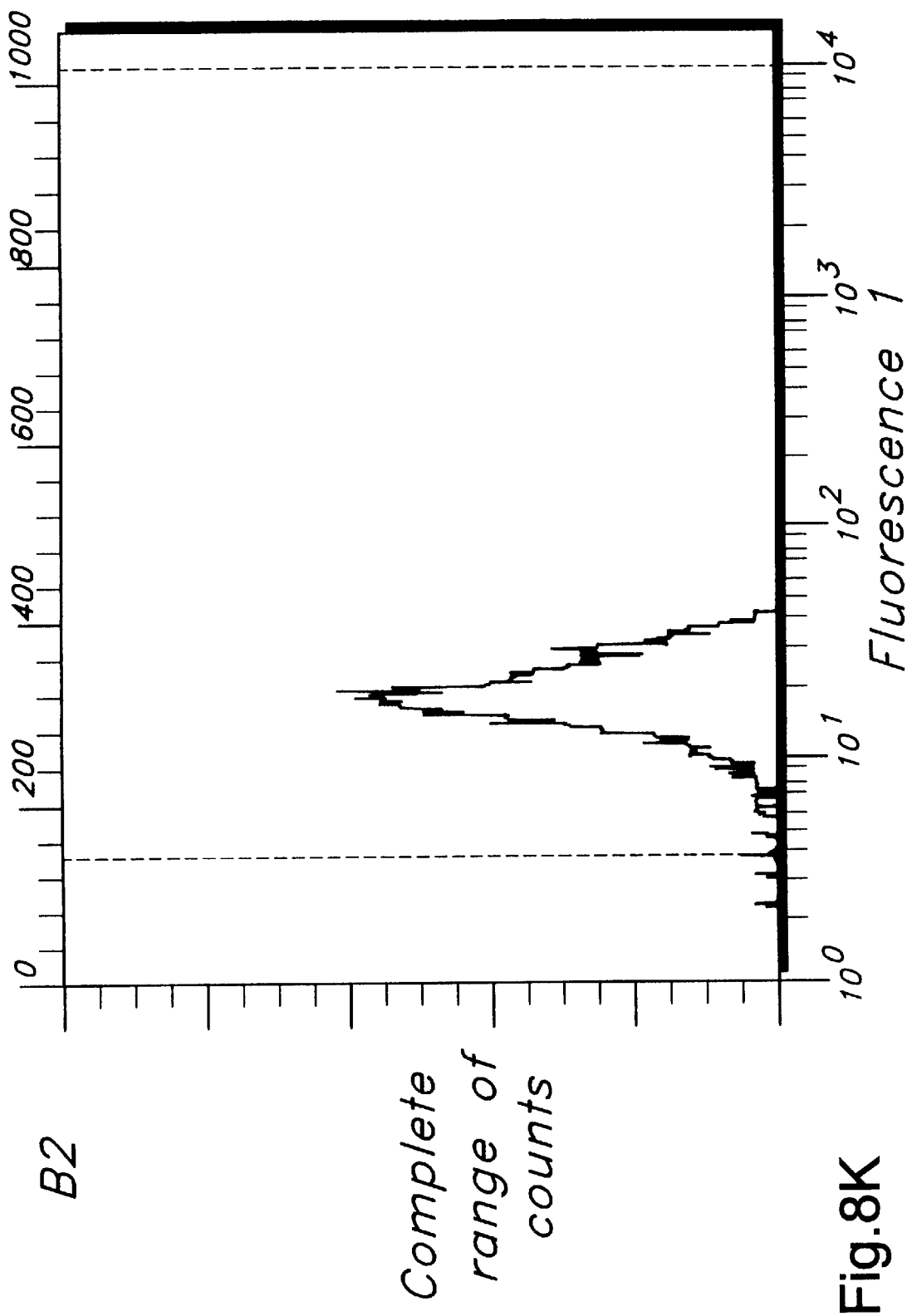
Figure 8L:
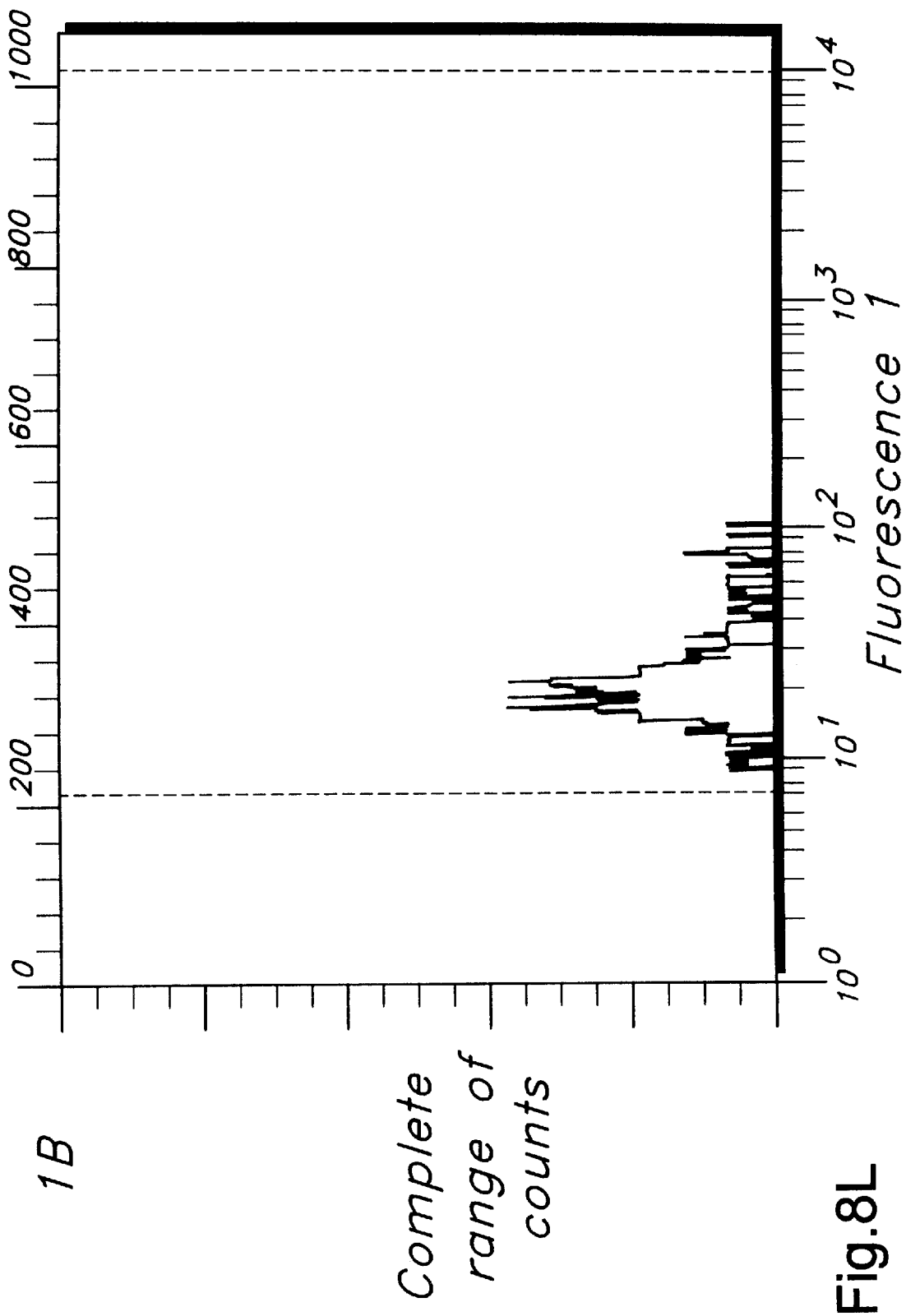

FIG. 7D shows a photograph of a section of a rat's testicle showing several seminiferous tubules. The spermatocytes labelled with L8 MAb are recognized at the periphery, revealing the expression of proteins of the invention by these cells.

XI. Extraction of the membrane protein of the plasma

The cultures are washed three times with PBS, then the cells are removed from the Petri dish, centrifuged at 6,500 rev/min for 10 seconds and solubilized either in 1% Triton X-100, 0.01% SDS, 2 mM of EDTA, 130 mM of NaCl, 10 mM of Tris-HCl (pH 7.4) or in 1% Triton X-114, 130 mM of NaCl, 10 mM of Tris-HCl (pH 7.4), passing five times through a G26 needle with a syringe and maintained for 30 minutes at 4° C. Two protease inhibitors are added to all the buffers, namely aprotinin (100 IU/ml) and phenylmethylsulphoxide (2 mM). The cellular lysates are centrifuged for 10 minutes at 13,000 rev/min.

When the soluble substance is extracted from Triton X-114, it is subjected to a phase separation, then the two phases are adjusted by adding either Triton X-114 or the buffer in order to obtain the same content of salts and surfactants in the different samples.

XII. Purification and sequencing of the protein reacting with the L8 monoclonal antibody The protein is purified from a crude preparation of adult rat liver membranes. These membranes are lyzed in the presence of Triton X-100 (1%) and SDS (0.1%). The lysate is centrifuged for 30 minutes at 20,000 g. The supernatant is deposited on a Sepharose—4B affinity column activated with CNBr and coupled with the L8 monoclonal antibody (L8MAb). After washing, the protein is eluted with 0.05 M diethylamine, pH 11.5, 0.1% Triton X-100. The preparation is then subjected to an anionexchange chromatography using a DEAE-cellulose column, then eluted with an NaCl gradient of 0 to 1 M. The elution peak is situated at 0.15 to 0.2 M NaCl. The eluate is precipitated with 10% TCA and analyzed in 8.5% SDS polyacrylamide gel. The protein is revealed by staining with amido black. It appears in the form of two bands of 85000 and 73000 Da.

For the sequencing, the gel band of 85000 Da is cut and dried. The gel is rehydrated then incubated in 150 $\mu$l of buffer containing 0.6 $\mu$g of porcine trypsin, for 4 hours 30 minutes at 37°.

The peptides formed are extracted from the gel by incubation for 20 minutes at 37° C. in 2×100 $\mu$l of 60% acetonitrile. They are separated through a C18 —HPLC column, then eluted. Six peaks were thus able to be collected, four corresponding to pure peptides; they were sequenced automatically using Edman's reaction.

XIII. Expression of the protein recognized by L8 MAb by the cells of hematopoietic tissues The thymus, spleen and lymph nodes of a rat are isolated and cut into small fragments in an RPMI 1640 culture medium. The hematopoietic cells isolated are released into the culture medium and collected. The bone marrow cells are obtained from rat femurs by washing the inner cavity with culture medium. The peripheral blood cells are collected on heparin. The erythrocytes are lyzed in a solution of ammonium chloride at 8.3 g/l and the remaining leukocytes are washed with PBS. The erythrocytes are isolated by centrifuging the heparinated blood at 1000 g for 10 minutes. The pellet collected is washed three times.

For the cytofluorimetry analysis, samples of 0.5 or 1×10$^6$ cells are incubated with the antibody for one hour at 4° C. After washing, the cells are incubated with the second antibody coupled with fluorescein for 30 minutes. The cells are then fixed with 1% of formaldehyde and analyzed with a FACS 400 cytofluorimetry laser. All the hematopoietic cells coming from all the hematopoietic organs are positive with the L8 MAb antibody by cytofluorimetry, namely the mononuclear cells, the granulocytes and the erythrocytes. This is illustrated by FIG. 8.

Figure 9:
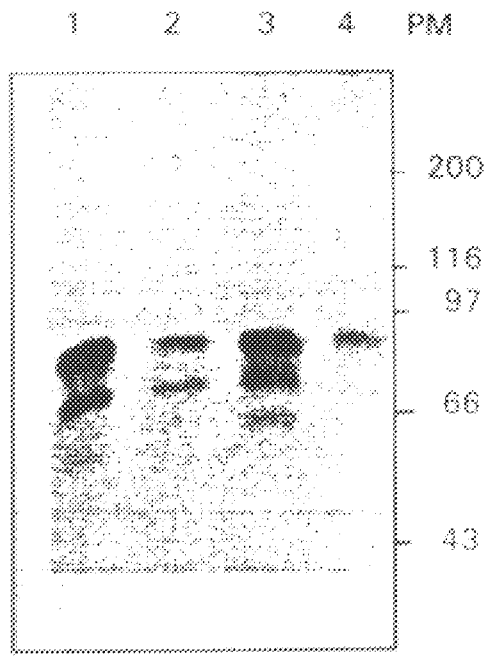
FIG. 9 shows the results of electrophoresis with thymus, RLEC, bone marrow and erythrocytes, with an indication of the molecular weight MW.

In order to analyze more precisely the protein recognized by L8 MAb at the level of these different cell types, it was immunoprecipitated as described above, from lysates of these different cells after iodination of their membrane. It is revealed by electrophoresis in SDS acrylamide gel. It appears, as shown by FIG. 9, that the band of 85000 Da is expressed by most of the cell types, which is evidence of a great homology of the protein from one cell type to another. On the other hand, specific characteristics make the molecule between these different cell types conspicuous at the level of the second band. This is particularly clear between erythrocytes and thymocytes (which correspond essentially to T lymphocytes); the erythrocytes only have one band of 85000 Da whereas the thymocytes have two bands at 85000 and 73000 Da.

XIV. Expression of the protein recognized by L8 MAb by bone marrow

Figure 10A:
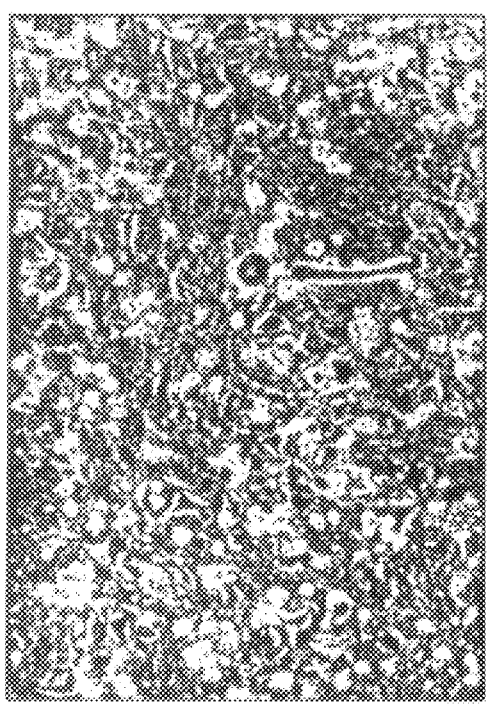
FIGS. 10A and 10B show the localization of L8 in the thymus and the stromal cells and, FIG. 11 shows a co-culture of hepatocytes.
Figure 10B:
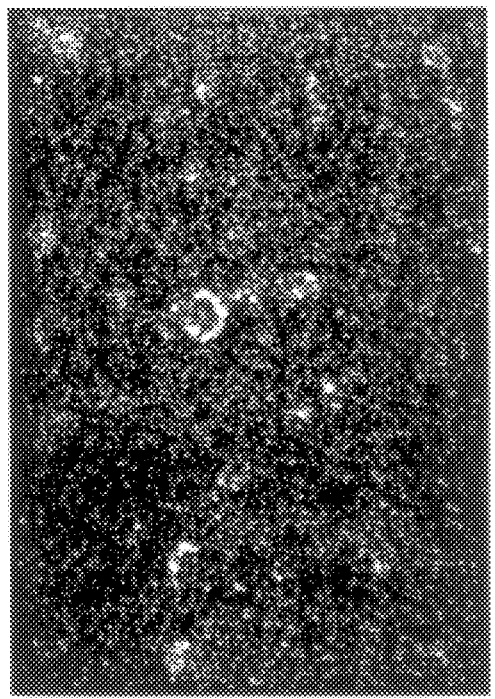

The bone marrow cells of a rat are collected from femurs by scraping the inner cavity. The culture of these cells takes place at 37° C. in DMEM medium with 10% of foetal calf serum and 5 $\mu$g/ml of insulin added to it. Only the stromal cells adhere after 18 hours, the other cells are eliminated. Generally, the long-term culture of stromal cells is initiated from 10×10$^6$ cells freshly isolated from marrow, placed in 5 ml of medium and in 25 cm$^2$ flasks. After 4 to 5 days, the cells have proliferated. The protein in these marrow stromal cells was revealed from these cultures by indirect immunolocalization. After washing, the cells are fixed in 4% of paraformaldehyde for 30 minutes at 4° C. The immunolocalization is carried out with L8 MAb and a second antibody coupled with fluorescein, as described above. In general, 3 types of cells are positive: the hematopoietic cells attached to the layer of stromal cells, the adipocytes and fibroendothelial cells (FIG. 10A and 10 B (FIG. 10A representing a view of bone marrow cells in phase contrast and FIG. 10B the immunolocalization of the L8 MAb at the level of the bone marrow cells)). Interestingly, it can be confirmed that there is an expression of the same protein at the level of the bone stroma and of the liver because the immunoprecipitation and the analysis by electrophoresis in acrylamide—SDS gel show the same two bands of 85000 and 73000 Da sometimes with a band of 64000 Da. The presence of the protein both at the level of the stroma and the hematopoietic cells reinforces the idea of a cellular communication signal just as in the liver.

XV. Co-culture of hepatocytes with bone marrow stromal cells

Figure 11:
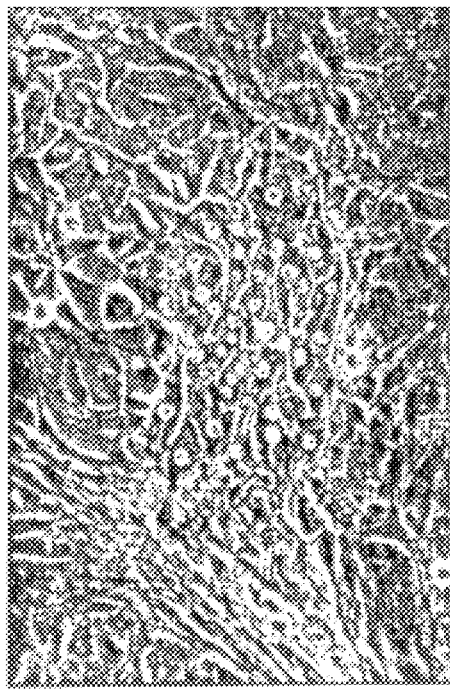

The hepatocytes isolated from rat's liver by enzymatic perfusion are seeded on a single layer already constituted by marrow stromal cells. In 2 to 4 hours the hepatocytes adhere, aggregate together, forming colonies of parenchymatous cells with perfectly recognizable morpho-logical characteristics, can be kept alive for about three weeks and actively secrete albumin. This confirms that the co-culture signal mediated by the LRP protein is common to the 2 tissue categories: liver and bone marrow (FIG. 11).

BIBLIOGRAPHICAL REFERENCES

1. Kleinman H. K. et al., Biochemistry 21:6188–6193, 1982.
2. Timpl R. et al., J. Biol. Chem. 254:9933–9937, 1979.
3. Hassel J. R. et al., J. Biol. Chem. 260:8098–8105, 1985.
4. Sargent T. D. et al., Proc. Natl. Acad. Sci. USA. 76:3256–3260, 1979.
5. Simon M. P. et al., J. Biol. Chem. 258:14567–14584, 1983.
6. Clavel C. et al., Int. J. Cancer. 44:548–553, 1989.
7. Leroux-Nicollet I. et al., Biochem. Res. Commun. 114:556–563, 1983.
8. Rheinwald J. G. et al., Cell. 6:317–330, 1975.
9. Gospodarowicz D. G. et al., Exp. Eye Res. 29:485–509, 1979.
10. Arruti C. et al., Exp. Cell. Res. 117:283–292, 1978.
11. Seglen P. O., Exp. Cell. Res. 76:25–30, 1973.
12. Guguen C. et al., Biochimie 57:1065–1071, 1975.
13. Guguen-Guillouzo C. et al., Exp. Cell Res. 143:47–54, 1983.
14. Williams G. M. et al., Exp. Cell Res. 69:106–112, 1971.
15. Morel-Chany E. et al., Eur. J. Cancer. 14:1341–1352, 1978.
16. Goding J. W. 1986, Academic Press Inc. London. 104–141. 1986, Godin J. W. editor.
17. Garcia Gonzalez M. S. et al., J. Immunol. Meth. 111:17–23, 1988.
18. Lescoat G. N., Cell Differ. 16:259–268, 1985. Guillouzo A. et al., C. Biol. Cell. 43:163–172, 1982.
19. Chirgwin J. M. et al., Biochemistry. 18:5294–5299, 1979. Andrews G. K. et al., J. Biol. Chem. 257:5148–5153, 1982. Eur. J. Biochem. 67:247–256, 1976.
20. Gordon H. et al., Am. J. Pathol. 12:545–551, 1936. Rubin K. et al., Exp. Cell Res. 163:127–138, 1986.
21. Clement B. et al. J. Biol. Chem. 264:12467–12471, 1989.
22. Laemmli U. K., Nature (Lond.) 227:680–685, 1970.
23. O'Farrell P., J. Biol. Chem. 250:4007–4021, 1975.
24. Bordier C., J. Biol. Chem. 256:1604–1607, 1981.

We claim:

1. An isolated and substantially purified protein having the following properties:

specifically reacts with a monoclonal antibody secreted by a clone having deposit number DSM ACC 2011, mediates cell-cell interactions, contains at least one peptide selected from the group consisting of SEQ ID NO:2, SEQ ID NO:3, SEQ ID NO:4, SEQ ID NO:5 and SEQ ID NO:6, is expressed in at least one mammalian tissue selected from the group consisting of the non-parenchymatous cells of liver, epithelial cell of the biliary ductules, endothelial cell, Ito cell and macrophage exocrine pancreas, testicles, a Sertoli cell of the seminiferous tubule and a spermatocyte between the eptotene stage and zygotene stage, ovaries, a mature ovocyte and follicular cells surrounding a mature ovocyte, hematopoietic tissue, bone marrow, stromal tissue of bone marrow, thymus, lymph node and spleen, myocyte, granulocyte, erythrocyte and lymphocyte, and is a glycoprotein with a single amino acid chain appearing as a dominant band with a molecular weight of about 85,000 daltons, or of about 73,000 daltons, as measured by SDS polyacrylamide gel electrophoresis, and having a pI of about 4.9 to 5.1 or having a pI of about 5.2, respectively.

2. A method of culturing hepatocytes comprising adding a composition comprising the protein of claim 1 to said hepatocytes.

3. The method of claim 2, wherein said hepatocytes are human hepatocytes.

4. A method of culturing hematopoietic cells comprising adding a composition comprising the protein of claim 1 to said hematopoietic cells.

5. A method of culturing stromal cells comprising adding a composition comprising the protein of claim 1 to said stromal cells.

6. A method of isolating the protein of claim 1 comprising:

contacting a cell membrane comprising said protein with said monoclonal antibody under conditions where said antibody specifically binds to said protein to form an antibody-protein complex, separating said complex from said membrane, and separating said protein from said complex.

7. An isolated nucleic acid molecule consisting of a nucleotide sequence encoding a peptide selected from the group consisting of SEQ ID NO:1, SEQ ID NO:2, SEQ ID NO:3, SEQ ID NO:4 and SEQ ID NO:5.

8. An isolated nucleic acid molecule consisting of a nucleotide sequence encoding a peptide selected from the group consisting of SEQ ID NO:1, SEQ ID NO:6, SEQ ID NO:3 and SEQ ID NO:7.

9. An isolated peptide selected from the group consisting of SEQ ID NO:1, SEQ ID NO:2, SEQ ID NO:3, SEQ ID NO:4 and SEQ ID NO:5.

10. An isolated peptide selected from the group consisting of SEQ ID NO:1, SEQ ID NO:6, SEQ ID NO:3, and SEQ ID NO:7.

11. An isolated and substantially purified protein produced by the process comprising the steps of:

solubilizing mammalian cell membranes to form a mixture, said mammalian cell membranes being obtained from a mammalian tissue selected from the group consisting of the non-parenchymatous cells of liver, epithelial cell of the biliary ductules, endothelial cell, Ito cell and macrophage, exocrine pancreas, testicles, a Sertoli cell of the seminiferous tubule and a spermatocyte between the leptotene stage and zygotene stage, ovaries, a mature ovocyte and follicular cells surrounding a mature ovocyte, hematopoietic tissue, bone marrow, stromal tissue of bone marrow, thymus, lymph node and spleen, myocyte, granulocyte, erythrocyte and lymphocyte, contacting said solubilized membranes with a monoclonal antibody secreted by a clone having deposit number DSM ACC 2011 under conditions whereby said antibody will specifically bind to a protein present in said solubilized membranes to form an antibody-protein conjugate, separating said conjugate from said mixture, separating said antibody from said conjugate to produce said protein;

said protein being capable of mediating cell-cell interactions; and said protein contains at least one peptide selected from the group consisting of SEQ ID NO:2, SEQ ID NO:3, SEQ ID NO:4, SEQ ID NO:5 and SEQ ID NO:6.

* * * * *